United States Patent
Nearman et al.

(10) Patent No.: US 9,295,378 B2
(45) Date of Patent: Mar. 29, 2016

(54) UNIVERSAL HANDLE

(75) Inventors: Howard S. Nearman, Pepper Pike, OH (US); Donald M. Voltz, Twinsburg, OH (US); Alon S. Aharon, Scarsdale, NY (US)

(73) Assignees: UNIVERSITY HOSPITALS OF CLEVELAND, Cleveland, OH (US); AMIN, TUROCY & WATSON, LLP, Cleveland, OH (US)

(*) Notice: Subject to any disclaimer, the term of this patent is extended or adjusted under 35 U.S.C. 154(b) by 1471 days.

(21) Appl. No.: 12/365,013

(22) Filed: Feb. 3, 2009

(65) Prior Publication Data
US 2009/0198111 A1  Aug. 6, 2009

Related U.S. Application Data

(60) Provisional application No. 61/026,096, filed on Feb. 4, 2008.

(51) Int. Cl.
*A61B 5/00* (2006.01)
*A61B 1/267* (2006.01)
(Continued)

(52) U.S. Cl.
CPC ............... *A61B 1/267* (2013.01); *G06Q 50/24* (2013.01); *A61F 9/008* (2013.01); *A61F 2009/00844* (2013.01); *Y10T 16/44* (2015.01)

(58) Field of Classification Search
CPC ............ G06F 19/3406; G06F 19/3418; G06F 19/321; A61B 1/00029; A61B 1/00032; A61B 1/045; A61B 1/0055; A61B 1/042; A61B 18/1482; A61B 1/00052; A61B 1/05; A61B 2017/00199; A61B 2017/00225; A61B 2017/00734; A61B 2017/00973; A61B 1/267; G02B 23/2484; G06Q 50/24
USPC ............................................. 600/188; 606/10
See application file for complete search history.

(56) References Cited

U.S. PATENT DOCUMENTS 5,256,149 A * 10/1993 Banik et al. ............... 604/164.01
5,976,158 A * 11/1999 Adams et al. ................. 606/140
(Continued)

FOREIGN PATENT DOCUMENTS

WO       02/056756 A2    7/2002

OTHER PUBLICATIONS

International Search Report and Written Opinion for PCT Application No. PCT/US2009/033101, mailed May 26, 2009, 7 pages.

*Primary Examiner* — William Thomson
*Assistant Examiner* — Shirley Jian
(74) *Attorney, Agent, or Firm* — Amin, Turocy & Watson, LLP

(57) ABSTRACT

The claimed subject matter provides systems and/or methods that facilitate employing a universal handle that provides various functionality and communicates with various network(s), device(s), and the like. The universal handle can be a handheld device that is auto-configured to implement rich functionality. Further, the universal handle can support remote diagnostic, prognostic, and control capabilities. Moreover, the universal handle can mate with disparate device(s), network(s), instrument(s), node(s), universal handle(s), and so forth to communicate data there between. Applications of the universal handle can be medically related, industry related, military related, etc. The universal handle can collect data directly and/or by controlling managed external device(s); the collected data can thereafter be analyzed, aggregated, stored, transmitted, outputted, and so forth by the universal handle.

19 Claims, 17 Drawing Sheets

(51) Int. Cl.
*G06Q 50/24* (2012.01)
*A61F 9/008* (2006.01)

(56) References Cited

U.S. PATENT DOCUMENTS

| | | | |
|---|---|---|---|
| 6,106,457 A * | 8/2000 | Perkins et al. | 600/175 |
| 6,393,431 B1 * | 5/2002 | Salvati et al. | |
| 6,430,430 B1 * | 8/2002 | Gosche | 600/410 |
| 6,527,784 B2 * | 3/2003 | Adams et al. | 606/140 |
| 6,613,060 B2 * | 9/2003 | Adams et al. | 606/157 |
| 6,770,027 B2 * | 8/2004 | Banik et al. | 600/146 |
| 6,790,178 B1 * | 9/2004 | Mault et al. | 600/300 |
| 6,847,854 B2 * | 1/2005 | Discenzo | 700/99 |
| 7,050,873 B1 * | 5/2006 | Discenzo | 700/99 |
| 7,097,615 B2 * | 8/2006 | Banik et al. | 600/146 |
| 7,149,756 B1 * | 12/2006 | Schmitt et al. | |
| 7,335,159 B2 * | 2/2008 | Banik et al. | 600/156 |
| 7,413,543 B2 * | 8/2008 | Banik et al. | 600/129 |
| 7,479,106 B2 * | 1/2009 | Banik et al. | 600/159 |
| 7,883,458 B2 * | 2/2011 | Hamel | 600/1 |
| 8,118,732 B2 * | 2/2012 | Banik et al. | 600/117 |
| 8,353,860 B2 * | 1/2013 | Boulais et al. | 604/43 |
| 8,357,148 B2 * | 1/2013 | Boulais et al. | 606/34 |
| 8,419,634 B2 * | 4/2013 | Nearman et al. | 600/188 |
| 8,435,172 B2 * | 5/2013 | Banik et al. | 600/159 |
| 8,460,184 B2 * | 6/2013 | Nearman et al. | 600/188 |
| 8,517,924 B2 * | 8/2013 | Banik et al. | 600/146 |
| 8,535,219 B2 * | 9/2013 | Smith et al. | 600/156 |
| 8,591,403 B2 * | 11/2013 | Yoshida et al. | 600/130 |
| 8,608,648 B2 * | 12/2013 | Banik et al. | 600/142 |
| 8,622,894 B2 * | 1/2014 | Banik et al. | 600/142 |
| 2002/0038075 A1 | 3/2002 | Tsai | |
| 2002/0198473 A1 * | 12/2002 | Kumar et al. | 600/595 |
| 2003/0061004 A1 * | 3/2003 | Discenzo | 702/182 |
| 2003/0069475 A1 * | 4/2003 | Banik et al. | 600/152 |
| 2004/0218810 A1 * | 11/2004 | Momma | 382/162 |
| 2005/0010098 A1 * | 1/2005 | Frigstad et al. | 600/407 |
| 2005/0052527 A1 * | 3/2005 | Remy et al. | 348/14.08 |
| 2005/0059894 A1 * | 3/2005 | Zeng et al. | 600/476 |
| 2005/0065400 A1 * | 3/2005 | Banik et al. | 600/109 |
| 2005/0154265 A1 * | 7/2005 | Miro et al. | 600/300 |
| 2005/0251228 A1 * | 11/2005 | Hamel | 607/60 |
| 2006/0276693 A1 | 12/2006 | Pacey | |
| 2006/0293563 A1 * | 12/2006 | Banik et al. | 600/117 |
| 2007/0030345 A1 * | 2/2007 | Amling et al. | 348/73 |
| 2008/0177143 A1 * | 7/2008 | Yoshida et al. | 600/130 |
| 2009/0198111 A1 * | 8/2009 | Nearman et al. | 600/300 |
| 2011/0243116 A1 * | 10/2011 | Endo et al. | 370/338 |
| 2011/0257481 A1 * | 10/2011 | Ogawa et al. | 600/109 |
| 2013/0204085 A1 * | 8/2013 | Alexander et al. | 600/109 |

* cited by examiner

UNIVERSAL HANDLE

CROSS-REFERENCE TO RELATED APPLICATIONS

This application claims the benefit of U.S. Provisional Patent Application Ser. No. 61/026,096 entitled "UNIVERSAL HANDLE" which was filed Feb. 4, 2008. The entirety of the aforementioned application is herein incorporated by reference.

BACKGROUND

Medical endoscopy has continued to advance with increasing sophistication in both camera and illumination technology. The area of airway management has also embraced technological advances in optics and light transmission resulting in development of numerous devices to assist a medical provider with placement of a breathing tube into the trachea of a patient requiring mechanical ventilatory assistance (e.g., endotracheal intubation).

An area of airway management which has not seen much advancement since the introduction of peroral endotracheal intubation in the 18th century is the design of the laryngoscopic instrument used to displace the tongue and allow for visualization of vocal cords and laryngeal aperture. A number of subtle changes have been implemented in these tools resulting in many different variations in the laryngoscopic blade. These devices, although quite varied in design, are placed into the oral cavity and used to forcefully move the tongue, mandible, and connected soft tissue out of the way allowing for visualization of the tracheal inlet. This maneuver can be highly stimulating to patients necessitating some form of anesthesia to tolerate its use. In addition, even with increasing levels of force applied to the device, there are patients with anatomical variants or pathologic conditions that do not allow direct visualization of the tracheal opening.

In the United States, it has been estimated that 10 million people undergo general anesthesia each year for a variety of operations. During the induction of general anesthesia, a significant percentage of patients require placement of an endotracheal tube along with mechanical ventilation to overcome cessation of breathing caused by anesthetic medications. The process of placing an endotracheal tube into the trachea varies in difficulty depending on a patient's body habitus, variations in normal anatomy, as well as variations in anatomic deviations as a result of numerous pathologic processes. Placement of the endotracheal tube depends both on the skills of the anesthesiologist as well as the instruments used to visualize the opening of the trachea. In a normal anesthetic situation, once a patient is placed under general anesthesia, a rigid laryngoscope can be placed into the mouth to displace the tongue allowing for exposure of the laryngeal aperture. Once the larynx is visualized, an endotracheal tube can be placed into the trachea and a high volume, low pressure cuff can be inflated to provide a seal between the endotracheal tube and the inner wall of the trachea. Numerous risks and complications can occur with the placement of an endotracheal tube, risks that increase in patients with abnormal body habitus (such as morbid obesity), or variations in normal anatomy as the result of congenital or pathologic conditions. Thus, anesthesiologists desire to quickly, reliably and safely place an endotracheal tube after anesthetic induction to mitigate chances of the patient becoming hypoxic (e.g., lack of oxygen in the blood) resulting in injury to systems in the body, especially the heart and the brain. For example, it has been estimated that intubation problems account for about one third of all deaths and serious injuries related to anesthesiology. In addition, many more patients are placed at risk outside the operating room. For instance, emergent placement of an endotracheal tube can be encountered when a patient experiences cardiac and/or respiratory arrest, both inside and outside the hospital setting. A challenge for anesthesiologists as well as other health care providers who have specialty training in the area of airway management is to place the endotracheal tube in a position far removed from where they are visualizing it (e.g., viewing from the mouth opening for traditional laryngoscopy).

Moreover, medical devices (e.g., including, in addition to or instead of the laryngoscope) oftentimes employ respective consoles that provide various functionality (e.g., display images, record/store results, . . . ) for each of the devices. However, these consoles can be bulky, expensive, etc., and thus, medical devices that leverage such consoles can be unavailable for use in various scenarios (e.g., while in transit on an ambulance, in a smaller clinic due to budgetary constraints, . . . ). Additionally, interaction with these medical devices (e.g. a user observing captured data to yield a diagnosis by way of one or more senses, . . . ) is typically limited to a user proximate to such devices (e.g., in the same room as the device, operator of the device, . . . ). Further, devices outside of the medical realm can encounter similar challenges.

SUMMARY

The following presents a simplified summary in order to provide a basic understanding of some aspects described herein. This summary is not an extensive overview of the claimed subject matter. It is intended to neither identify key or critical elements of the claimed subject matter nor delineate the scope thereof. Its sole purpose is to present some concepts in a simplified form as a prelude to the more detailed description that is presented later.

The claimed subject matter relates to systems and/or methods that facilitate employing a universal handle that provides various functionality and communicates with various network(s), device(s), and the like. The universal handle can be a handheld device that is auto-configured to implement rich functionality. Further, the universal handle can support remote diagnostic, prognostic, and control capabilities. Moreover, the universal handle can mate with disparate device(s), network(s), instrument(s), node(s), universal handle(s), and so forth to communicate data there between. Applications of the universal handle can be medically related, industry related, military related, etc. The universal handle can collect data directly and/or by controlling managed external device(s); the collected data can thereafter be analyzed, aggregated, stored, transmitted, outputted, and so forth by the universal handle.

According to one or more aspects of the claimed subject matter, improved visualization associated with intubation can be yielded. A dynamically articulating laryngoscope blade can be controlled to configure to normal anatomic variants and pathologic abnormalities to facilitate placing of an endotracheal tube into a patient's trachea. Further, cameras can be integrated into and/or mounted upon the dynamically articulating laryngoscope blade. The cameras can enable stereoscopic visualization of the laryngeal aperture allowing for depth perception. Moreover, the cameras can be moved independently of the blade allowing for optimal viewing of the laryngeal opening.

In accordance with various aspects of the claimed subject matter, data observed from the oral cavity can be retained in a data store. For example, videos and/or images can be collected within the data store associated with an airway management apparatus (e.g., laryngoscope). Further, the videos and/or images can be archived when the apparatus is placed in a cradle (e.g., uploaded to a hospital server). Additionally or alternatively, the videos and/or images can be retained upon memory (e.g., flash) that can be removed from the apparatus (e.g., and included in a patient's file, used for training/documentation purposes, . . . ).

Pursuant to one or more aspects of the claimed subject matter, collected data can be wirelessly transmitted to a disparate device for real time presentation. For example, the videos and/or images can be wireless transmitted from the apparatus to a disparate device capable of presenting a corresponding output. Therefore, while the laryngoscope is positioned within the oral cavity, feedback can be output to the user of the laryngoscope (and/or any disparate user). It is contemplated that any type of wireless communication technology can be leveraged to communicate the collected data to the disparate device. Further, control of the articulating blade and/or cameras can be obtained from the disparate device via the wireless communication.

The following description and the annexed drawings set forth in detail certain illustrative aspects of the claimed subject matter. These aspects are indicative, however, of but a few of the various ways in which the principles of such matter may be employed and the claimed subject matter is intended to include all such aspects and their equivalents. Other advantages and novel features will become apparent from the following detailed description when considered in conjunction with the drawings.

BRIEF DESCRIPTION OF THE DRAWINGS

FIG. 1 illustrates a block diagram of an example system that provides various functionality and communicates with various network(s), device(s), and the like.

Figure 1:
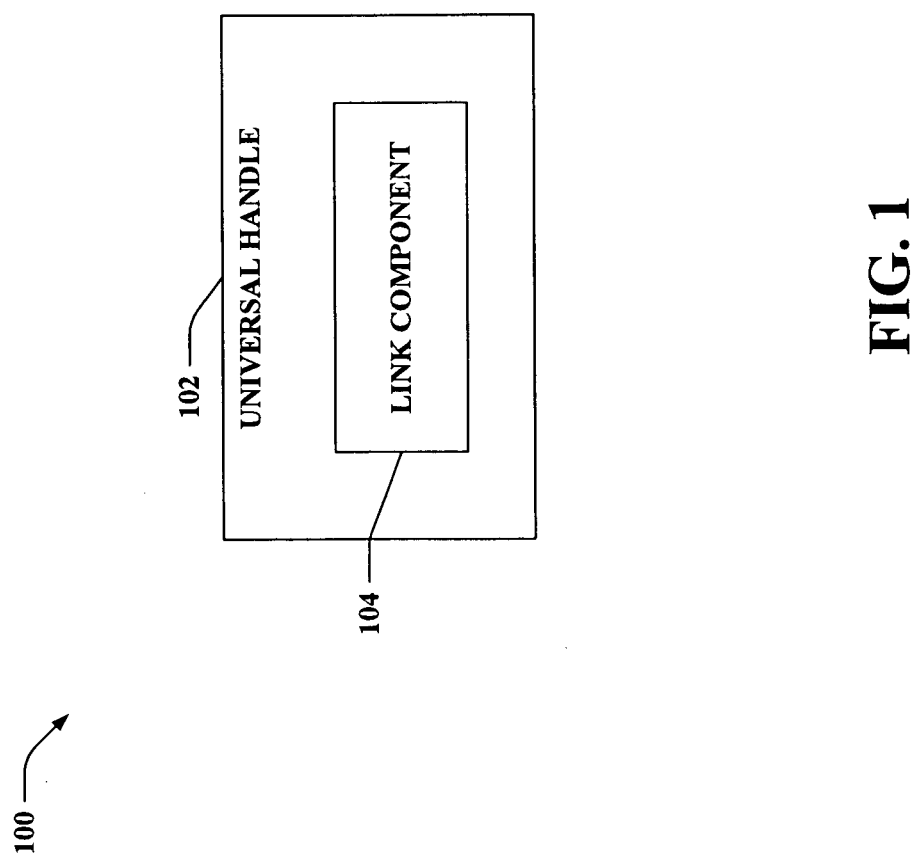

Appendix A describes various exemplary aspects associated with a universal handle—this appendix is to be considered part of the specification of the subject application.

DETAILED DESCRIPTION

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation.

As utilized herein, terms "component," "system," and the like are intended to refer to a computer-related entity, either hardware, software (e.g., in execution), and/or firmware. For example, a component can be a process running on a processor, a processor, an object, an executable, a program, and/or a computer. By way of illustration, both an application running on a server and the server can be a component. One or more components can reside within a process and a component can be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips, . . . ), optical disks (e.g., compact disk (CD), digital versatile disk (DVD), . . . ), smart cards, and flash memory devices (e.g., card, stick, key drive, . . . ). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter. Moreover, the word "exemplary" is used herein to mean serving as an example, instance, or illustration. Any aspect or design described herein as "exemplary" is not necessarily to be construed as preferred or advantageous over other aspects or designs.

Now turning to the figures, FIG. 1 illustrates an example system 100 that provides various functionality and communicates with various network(s), device(s), and the like. The system 100 includes a universal handle 102 that is a handheld device that can be auto-configured to implement certain functionalities and can support remote diagnostic, prognostic, and control capabilities. The universal handle 102 can be employed in a variety of disparate scenarios. For instance, the universal handle 102 can be leveraged in medical scenarios (e.g. consumer type device to be employed at home, medical provider type device that can integrate with a variety of devices, instruments, and the like such as flexible scope driven device(s) and/or robotic medical apparatuses, . . . ). Pursuant to another illustration, the universal handle 102 can be supported in various industries (e.g., airline, structural material inspection, . . . ) and/or leveraged in connection with military applications. It is to be appreciated, however, that the claimed subject matter is not limited to the aforementioned scenarios.

The universal handle 102 can further include a link component 104 that initiates communication and/or transfers data with disparate device(s), network(s), instrument(s), component(s), node(s), and so forth. For example, the link component 104 can transmit data collected by the universal handle 102 and/or receive data directed to the universal handle 102. The link component 104 can enable communication to be effectuated via one or more of wireless connection(s), wired connection(s), a combination thereof, and so forth. According to an illustration, the universal handle 102 can physically connect to a disparate device that can provide additional functionality. The universal handle 102 and the disparate device can be directly coupled (e.g., physical and electrical interlock there between), physically connected via a wire, and so forth. Pursuant to another example, the universal handle 102 and the disparate device can communicate via a wireless connection; thus, the link component 104 (and/or the universal handle 102) can include various components for wireless transmission and reception (e.g., antennas, processor(s), modulator(s), multiplexer(s), demodulator(s), demultiplexer(s), . . . ). Moreover, the disparate device, for instance, can collect data and send the collected data to the universal handle 102, which can receive such data via utilizing the link component 104. Additionally or alternatively, control signal(s) can be obtained via the link component 104, and the control signal(s) can manage operation associated with the universal handle 102.

The link component 104 can enable connecting to a variety of differing device(s), network(s), instrument(s), component(s), node(s), etc. For instance, the link component 104 can connect to substantially similar link component(s) of substantially similar universal handle(s); thus, data can be transferred between universal handles. According to another illustration, the link component 104 can allow for connecting to display(s), server(s), data store(s), processing center(s), on-call doctor(s), military commanders, specialist(s), call center(s), and so forth. For instance, the link component 104 can allow for communicating via any type of network and any type of connection to such networks. Moreover, the link component 104 can receive feedback, which can but need not be employed to control the universal handle 104 and/or a disparate linked device, for example.

Various functionality can be provided by the universal handle 102. For instance, the universal handle 102 can be a phone such as a cellular phone that can operate upon a cellular network; hence, the universal handle 102 can provide typical features associated with such phones (e.g., conferencing, call holding, call merging, caller ID, voice dialing, call forwarding, . . . ). For instance, a physician or a patient can employ the universal handle 102 to talk in real time. According to another example, the universal handle 102 can collect, compress, store, distribute, reconstruct, replay, etc. various multimedia data. Moreover, the universal handle 102 can support Internet connectivity (e.g., browsing, searching, streaming, downloading, uploading, etc. of data, . . . ), emailing, messaging, and the like. Additionally, the universal handle 102 can utilize various software applications. The aforementioned examples are provided for illustration purposes and the claimed subject matter is not so limited.

The universal handle 102 can display a variety of pull down menus that can be employed by users. For instance, a technician can select an option from the menus that can cause the universal handle 102 to enter a mode that provides rich functionality corresponding to the menu choice; this functionality can enable the universal handle 102 to perform diagnostics, prognostics, and so forth. Moreover, the menu choices can be tailored based upon user profile (e.g., sophistication of the user, spoken language(s), cognitive load able to be handled, . . . ); this profile can also be communicated (e.g., to a physician when a consumer version of the universal handle 102 is employed, . . . ). Further, the universal handle 102 can enable visualizing and/or interacting with any type of topography (e.g., display rendered from image data collected by a scope, computer desktop, . . . ). The topography can be generated based upon data collected directly by the universal handle 102 and/or any disparate source.

Figure 2:
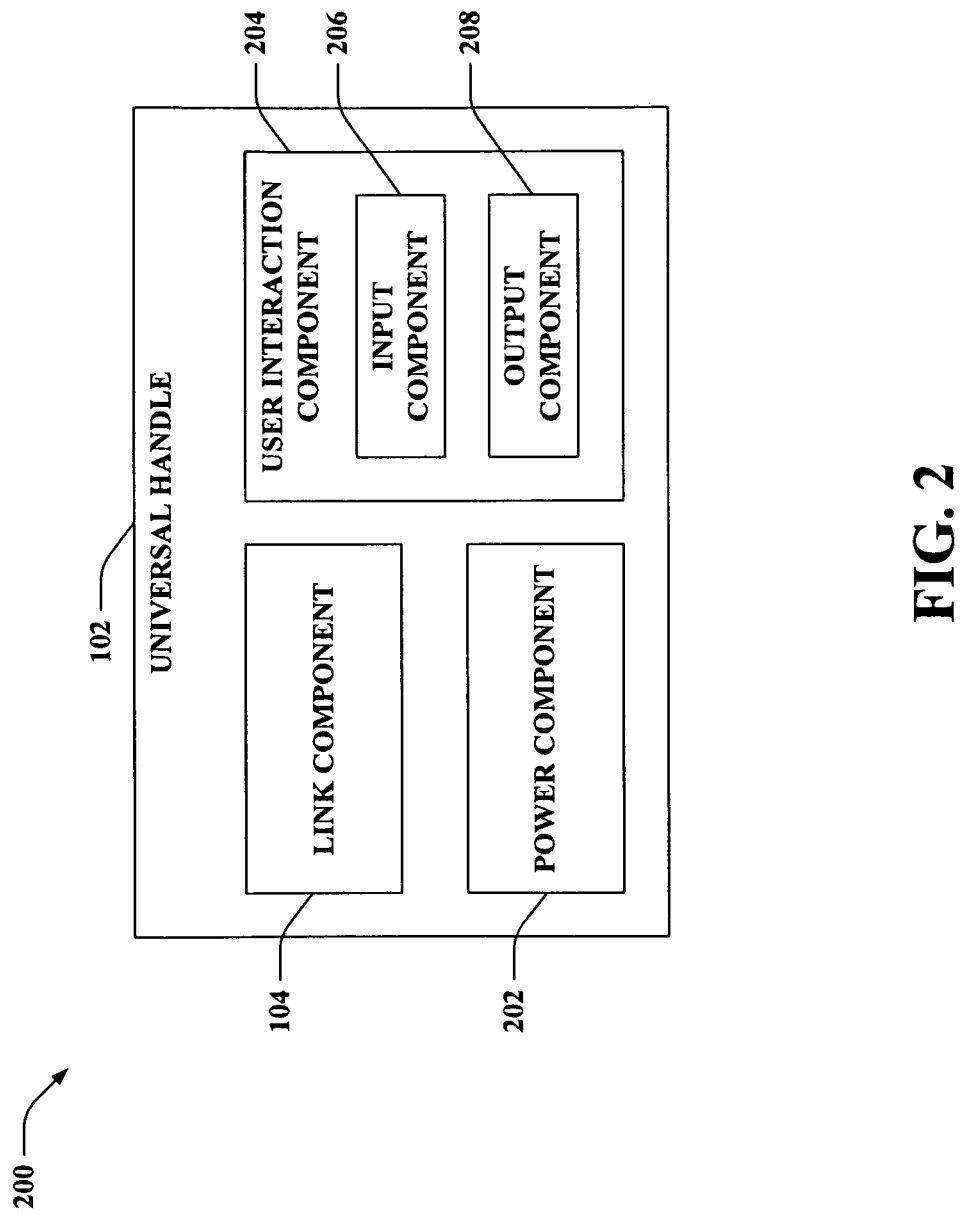
FIG. 2 illustrates a block diagram of an example system that enhances user interaction with a handheld device.

With reference to FIG. 2, illustrated is an example system 200 that enhances user interaction with a handheld device. The system 200 includes the universal handle 102, which can further comprise the link component 104. Moreover, the universal handle 102 can include a power component 202 that supplies power to the universal handle 102. Additionally or alternatively, the power component 202 can provide power to a device coupled to the universal handle 102 via the link component 104 (e.g. physically connected, coupled by way of wireless connection, . . . ); thus, according to an illustration, a scope attached to the universal handle 102 can be powered by the power component 202 of the universal handle 102 (however, it is contemplated that the scope can leverage a power supply coupled thereto in addition to or instead of the power component 202). For instance, the power component 202 can be one or more batteries (e.g., rechargeable, non-rechargeable, removable, non-removable . . . ).

The universal handle 102 can further include a user interaction component 204 that enables a user that employs the universal handle 102 to interact therewith. The user interaction component 204 can include an input component 206 and an output component 208. The input component 206 can receive any type of user input. Additionally or alternatively, the input component 206 can monitor, sense, evaluate, analyze, measure, and so forth a condition, parameter, state, value, and the like. For example, the input component 206 can include a pointing device (e.g. touchscreen, mouse, trackball, touchpad, tablet that uses a stylus, light pen, eye tracking device, joystick, . . . ), a keyboard, an imaging device (e.g. camera, scanner, barcode reader, . . . ), a microphone, a sensor (e.g., thermometer, electromagnetic, mechanical, chemical, radiation, acoustic, motion, orientation, . . . ), a combination thereof, etc.

Further, the output component 208 can yield an output to a user of the universal handle 102. For instance, the output component 208 can provide an output that can be perceived by any sense(s) of the user (e.g., sight, sound, touch, taste, smell). Pursuant to an example, the output component 208 can include a display, a speaker, a printer, a combination thereof, and so forth. According to an illustration, the input component 206 can be a touchscreen that can obtain user input, and output can also be provided via the touchscreen (e.g. the touchscreen can also be at least a portion of the output component 208). Moreover, in the scenario where two universal handles communicate (e.g. directly, via a network connection, located proximate each other, positioned at great distances from one another, . . . ), a first universal handle can collect data and serve the data to a second universal handle; the second universal handle can thereafter display, yield sound, print, etc. the data via a respective output component (e.g., the output component 208) and/or obtain input data via a respective input component (e.g., the input component 206) that can be stored, transmitted (e.g., to the first universal handle, a remote data repository, a central processing center, . . . ), and so forth.

Moreover, the user interaction component 204 can provide various types of user interfaces to facilitate interaction between a user and any component of and/or coupled to the universal handle 102. The user interaction component 204 can provide one or more graphical user interfaces (GUIs), command line interfaces, and the like. For example, a GUI can be rendered that provides a user with a region or means to load, import, read, etc., data, and can include a region to present the results of such. These regions can comprise known text and/or graphic regions comprising dialogue boxes, static controls, drop-down-menus, list boxes, pop-up menus, edit controls, combo boxes, radio buttons, check boxes, push buttons, and graphic boxes. In addition, utilities to facilitate the presentation such as vertical and/or horizontal scroll bars for navigation and toolbar buttons to determine whether a region will be viewable can be employed. For example, the user can interact with one or more of the components coupled to the universal handle 102.

The user can also interact with the regions to select and provide information via various input component(s) 206 devices such as a mouse, a roller ball, a keypad, a keyboard, a pen and/or voice activation, for example. Typically, a mechanism such as a push button or the enter key on the keyboard can be employed subsequent entering the information in order to initiate the search. However, it is to be appreciated that the claimed subject matter is not so limited. For example, merely highlighting a check box can initiate information conveyance. In another example, a command line interface can be employed. For example, the command line interface can prompt (e.g., via a text message on a display and an audio tone) the user for information via providing a text message. The user can than provide suitable information, such as alpha-numeric input corresponding to an option provided in the interface prompt or an answer to a question posed in the prompt. It is to be appreciated that the command line interface can be employed in connection with a GUI and/or API. In addition, the command line interface can be employed in connection with hardware (e.g., video cards) and/or displays (e.g., black and white, and EGA) with limited graphic support, and/or low bandwidth communication channels.

Figure 3:
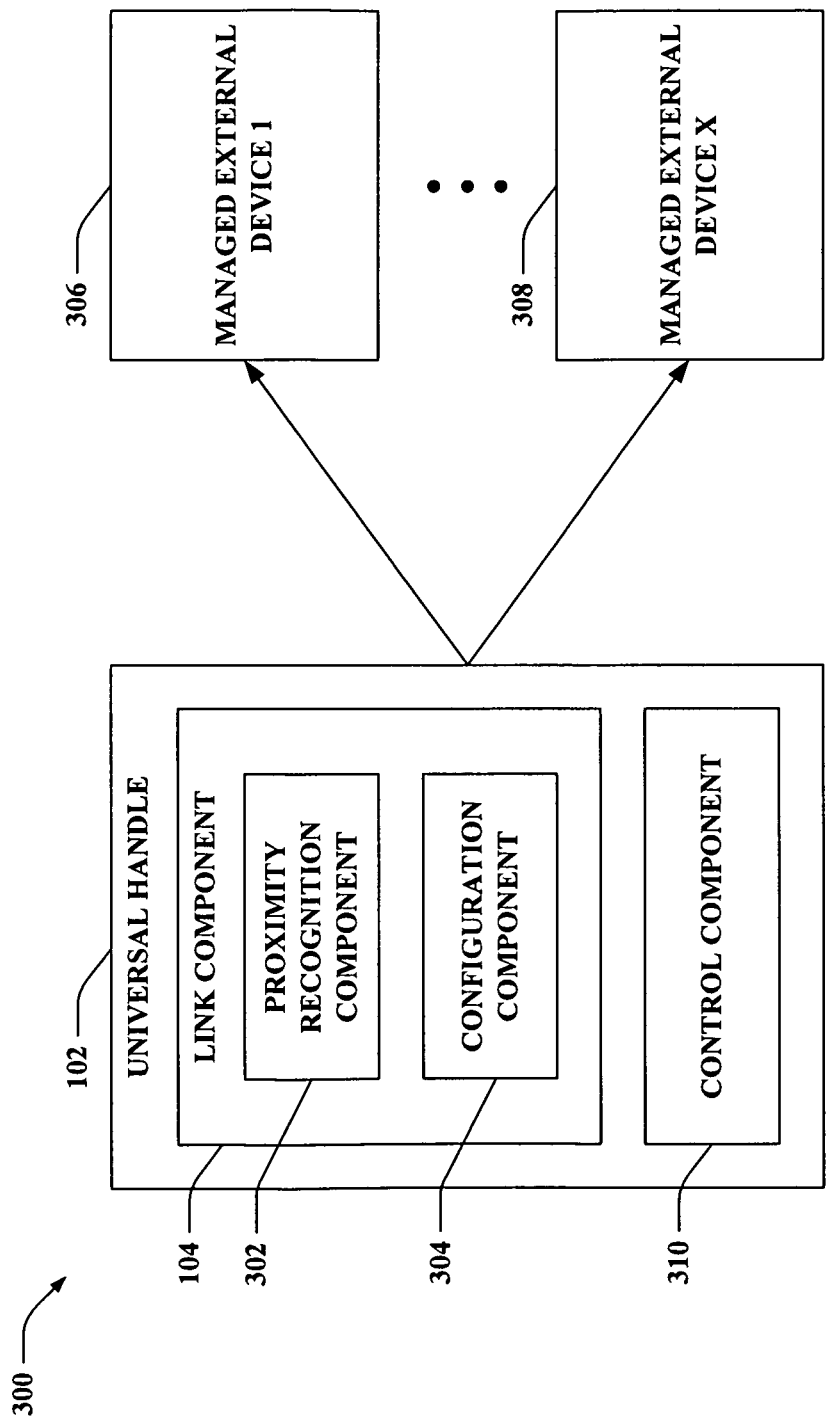
FIG. 3 illustrates a block diagram of an example system that enables mating a universal handle with a variety of instruments.

Referring to FIG. 3, illustrated is an example system 300 that enables mating a universal handle with a variety of instruments. The system 300 includes the universal handle 102, which can further comprise the link component 104. The link component 104 can further include a proximity recognition component 302 and/or a configuration component 304 that can enable identifying and initializing communication with one or more managed external devices (e.g., managed external device 1 306, . . . , managed external device X 308, where X can be substantially any integer). It is contemplated that the universal handle 102 can connect with one or more managed external devices 306-308 at any particular time; further, such connections can be direct physical connections, wired connections, wireless connections, and so forth. Moreover, the universal handle 102 can include a control component 310 that can control operation associated with mated managed external device(s) 306-308.

The proximity recognition component 302 can identify managed external device(s) 306-308 within range of the universal handle 102. According to an illustration, if a doctor who employs the universal handle 102 enters an operating room, the proximity recognition component 302 can determine whether any managed external devices 306-308 (e.g., scope, display, . . . ) are located in the operating room. Further, the proximity recognition component 302 can decipher characteristics associated with the managed external devices 306-308 determined to be within proximity; the characteristics can be evaluated based upon a received communication, retrieved from memory (e.g., of the universal handle 102 and/or from a remotely located repository). Pursuant to another example, the proximity recognition component 302 can provide Bluetooth sniffing capabilities; thus, the proximity recognition component 302 can identify any device within proximity that can be triaged with the universal handle 102, which can enable creating a dynamic system that leverages nearby devices that act in concert with one another. It is contemplated, however, that proximity of the universal handle 102 to the managed external devices 306-308 need not be determined (e.g. under the scenario where the universal handle 102 physically interlocks with a managed external device, . . . ).

The configuration component 304 can enable initializing interaction between the universal handle 102 and one or more managed external devices 306-308. For instance, the configuration component 304 can automatically configure the universal handle 102 and/or the managed external device(s) 306-308 for interaction. The configuration component 304 can configure a managed external device (e.g. the managed external device 1 306, . . . ) in response to user input, a command received from a remote source (e.g., via the link component 104), automatically, upon occurrence of a triggering condition, and so forth.

According to another illustration, the link component 104, the proximity recognition component 302, and/or the configuration component 304 can enable connecting and communicating with one or more disparate universal handles, which can be substantially similar to the universal handle 102. Upon forming these connections, a mesh network of universal handles can be yielded. Social networking can be built upon the mesh network, for instance.

The control component 310 can control operations associated with one or more managed external devices 306-308. The control component 310 can control operation subsequent to initialization by the configuration component 304, for example. According to an illustration, the control component 310 can be a servomotor; however, the claimed subject matter is not so limited. Pursuant to another example, the control component 310 can yield a command that can be transmitted to the one or more managed external devices 306-308, and the receiving managed external device(s) 306-308 can implement such command.

Additionally, although not shown, the universal handle 102 can include a light source (e.g., which can be utilized by the managed external device(s) 306-308), optics to reconstitute images, and so forth. For example, the light source can be one or more light emitting diodes (LEDs). Following this example, the LEDs can operate at one or more wavelengths (e.g., one LED operating at one wavelength can be employed, one or more LEDs each operating at more than one wavelength can be utilized, more than one LED each of which operate at one wavelength can be used, . . . ). For example, an application chosen in a menu of the universal handle 102 can initiate selection of a most appropriate light source and/or wavelength to maximize data gathering The universal handle 102 can mate with a variety of managed external devices 306-308. A managed external device (e.g., the managed external device 1 306, the managed external device X 308, . . . ) can be a medical device, a device utilized in various industries, a device employed in military settings, and so forth. Depending upon the application, the universal handle 102 can provide complementary functionality.

The managed external device 306-308 can be a flexible scope driven device. Examples of flexible scope driven devices include devices employed for laryngoscopy, colonoscopy, sigmoidoscopy, bronchoscopy, autoscopy, mediastinoscopy, peritoneal endoscopic visualization, thoracic endoscopic visualization, transesophageal echocardiography (e.g., 2D, 3D), surface echocardiography, intra-uterine ultrasound (e.g., 2D, 3D, to provide real time monitoring during delivery process of a baby, . . . ), abdominal ultrasound (e.g. transperitoneal ultrasound examination during trauma evaluation, . . . ), and so forth. Accordingly, the flexible scope driven device can include a transducer that can be controlled via the control component 310; thus, the flexible scope driven device can yield image data for instance, which can be provided to the universal handle 102 (e.g., for outputting, storing, processing, transmitting to a remote site, . . . ). It is to be appreciated, however, that the claimed subject matter is not so limited.

Moreover, the managed external device 306-308 can be a robotics related medical device. Hence, the universal handle 102 can drive a robotic arm for applications including minimally invasive thoracic and laparoscopic surgeries. For instance, the universal handle 102 can mate with one or more trocars, a robotic arm (e.g., the universal handle 102 can control elbow and/or wrist movements of the robotic arm), and so forth. According to an example, the universal handle 102 can display a graphic that represents actual position, orientation, etc. of the robotic arm; the user of the universal handle 102 can manipulate the position, orientation, etc. depicted in the graphic on the display, which can cause a signal to be transmitted to the robotic arm to effectuate altering the actual position, orientation, etc.

Pursuant to other illustrations, the universal handle 102 can couple with managed external device(s) 306-308 utilized in a various industries. For instance, the managed external device 306-308 can be a borescope or chamberscope employed in connection with the airline industry. Thus, engines, gears, turbines, etc. of an airplane can be inspected via the borescope and provided to the universal handle 102, which can thereafter transmit data to a remote location (e.g. to an engineer located a great distance away). Further, control signals can be received by the universal handle 102 from the remote location to impact operation of the universal handle 102 and/or the managed external device 306. Additionally or alternatively, the managed external device(s) 306-308 can include instruments utilized for structural materials inspections (e.g., buildings, bridges, support structures, mechanical devices, . . . ).

By way of another example, the managed external device 306-308 can be employed in a military application. The universal handle 102 can mate with a snake cam (e.g., via a cable). Thus, information can be collected by the snake cam and provided to the universal handle 102; thereafter, the universal handle 102 can send the information to command (e.g., for planning purposes).

Figure 4:
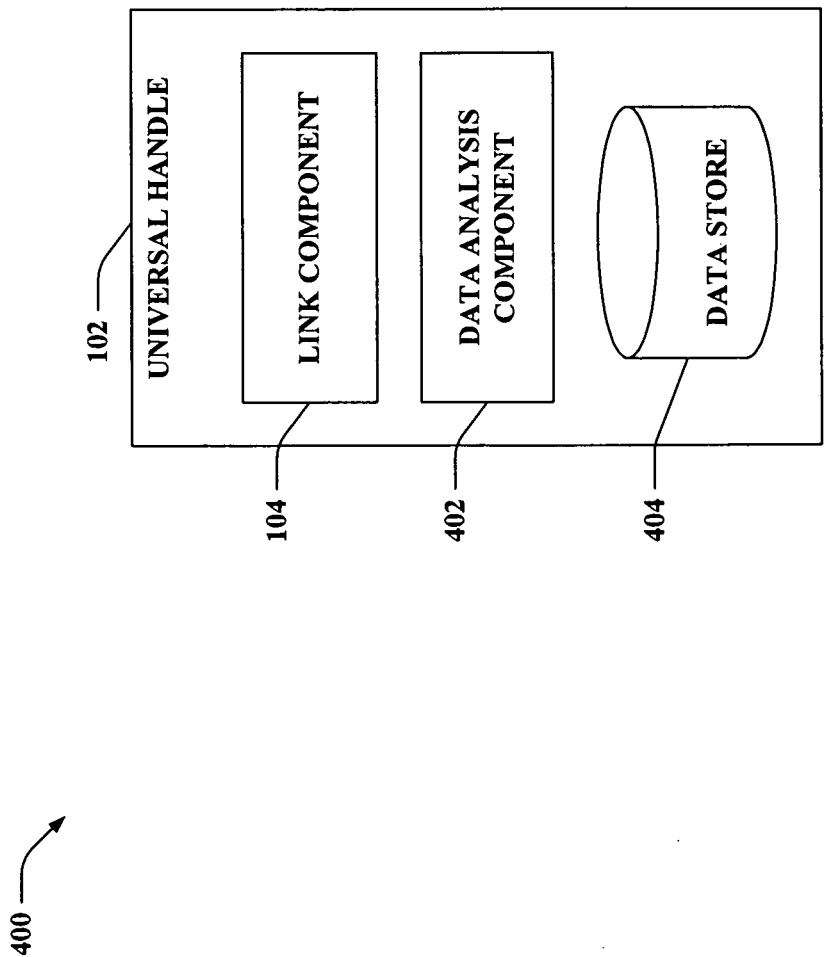
FIG. 4 illustrates a block diagram of an example system that employs data obtained and/or generated by the universal handle.

With reference to FIG. 4, illustrated is an example system 400 that employs data obtained and/or generated by the universal handle 102. The universal handle 102 can include the link component 104 to mate with other instrument(s), network(s), universal handle(s), and so forth. Moreover, the universal handle 102 can include a data analysis component 402 and a data store 404.

The data analysis component 402 can process data obtained by the universal handle 102. For example, the data analysis component 402 can perform pattern recognition. Following this example, data can be collected directly by the universal handle 102, received from a managed external device (e.g., laryngoscope blade, . . . ), and/or obtained from any other source; thereafter, the data analysis component 402 can perform pattern recognition upon the data to yield a diagnosis. By way of illustration, the universal handle 102 can include a camera (e.g., input component 206 of FIG. 2) that can be utilized to capture a picture of a rash; the data analysis component 402 can evaluate the picture to diagnose a medical condition associated with the rash, decide whether to instruct the user to seek additional medical attention based upon the diagnosis, and so forth. The data analysis component 402 can enable the universal handle 102 to perform a first round of evaluation; based upon the preliminary scan of information by the data analysis component 402, a referral to a nearest, most available physician who can address a diagnosed problem can be generated, for example. In general, performance of pattern recognition can enable diagnosing standard conditions quickly, efficiently, and accurately while mitigating need for unneeded referrals. The universal handle 102 can enable diagnosing a patient from the patient's home (e.g., universal handle 102 itself can perform the evaluation based upon collected data and/or push the data to some other location). The data analysis component 402 can additionally or alternatively aggregate data obtained by the universal handle 102 (and/or any number of disparate sources of data). Further, the data analysis component 402 can perform real time updating of records, forecasting of future conditions, trending evaluations, and the like. According to another example, the data analysis component 402 can be a smart device that can recognize, through pattern recognition, a target (e.g., in the case of being associated with a laryngoscope the target can be the glottic opening, . . . ) and guide a tube to that target.

Pursuant to an example, the universal handle 102 can be a repository and collector of medical information. The universal handle 102 can collect substantially any type of medical data (e.g., directly, with a disparate apparatus, . . . ). Thus, for instance, a user can use a machine to test her blood sugar, and this machine can transmit the results to the universal handle 102 (e.g., which can receive the information via the link component 104). The universal handle 102 can further disseminate the data related to the results (e.g., to a processing center, on-call doctor, . . . ) via the link component 104 (e.g., over a network connection, . . . ). Further, the universal handle 102 can analyze the received information with the data analysis component 402 and/or retain the information in the data store 404.

The data store 404 can be, for example, either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable programmable ROM (EEPROM), or flash memory. Volatile memory can include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM). The data store 402 of the subject systems and methods is intended to comprise, without being limited to, these and any other suitable types of memory. In addition, it is to be appreciated that the data store 404 can be a server, a database, a hard drive, and the like. According to an illustration, the data store 404 can be a flash drive coupled to the universal handle 102 (e.g., the flash drive can retain collected, received, etc. data); however, the claimed subject matter is not so limited.

Although depicted as being included in the universal handle 102, it is to be appreciated that the data analysis component 402 and/or the data store 404 can be located at a disparate network node. For instance, the universal handle 102 and any number of additional universal handles can connect to a call center (and/or server, processing center associated with an on-call doctor, expert, commander, . . . ), which can include the data analysis component 402 and/or the data store 404. Accordingly, data obtained, generated, etc. by the universal handle 102 can be forwarded to the call center for evaluation by the data analysis component 402, retention by the data store 404, and so forth.

By way of example, the universal handle 102 can enable retaining dynamic medical records. For instance, data related to any procedure can be collected by the universal handle 102 and converted into a patient's dynamic medical record. The dynamic medical record can be stored upon the universal handle 102 and/or at a remote location (e.g., upon one or more servers, . . . ). The dynamic medical record can be updated concurrently by a plurality of universal handles. Moreover, the dynamic medical record can be continuously updating in real time. The dynamic medical record can include studies, reconstructions, images, sounds, values, and/or any types of data pertaining to the patient. Moreover, key diagnoses can be generated based upon information included in the dynamic medical records.

Figure 5:
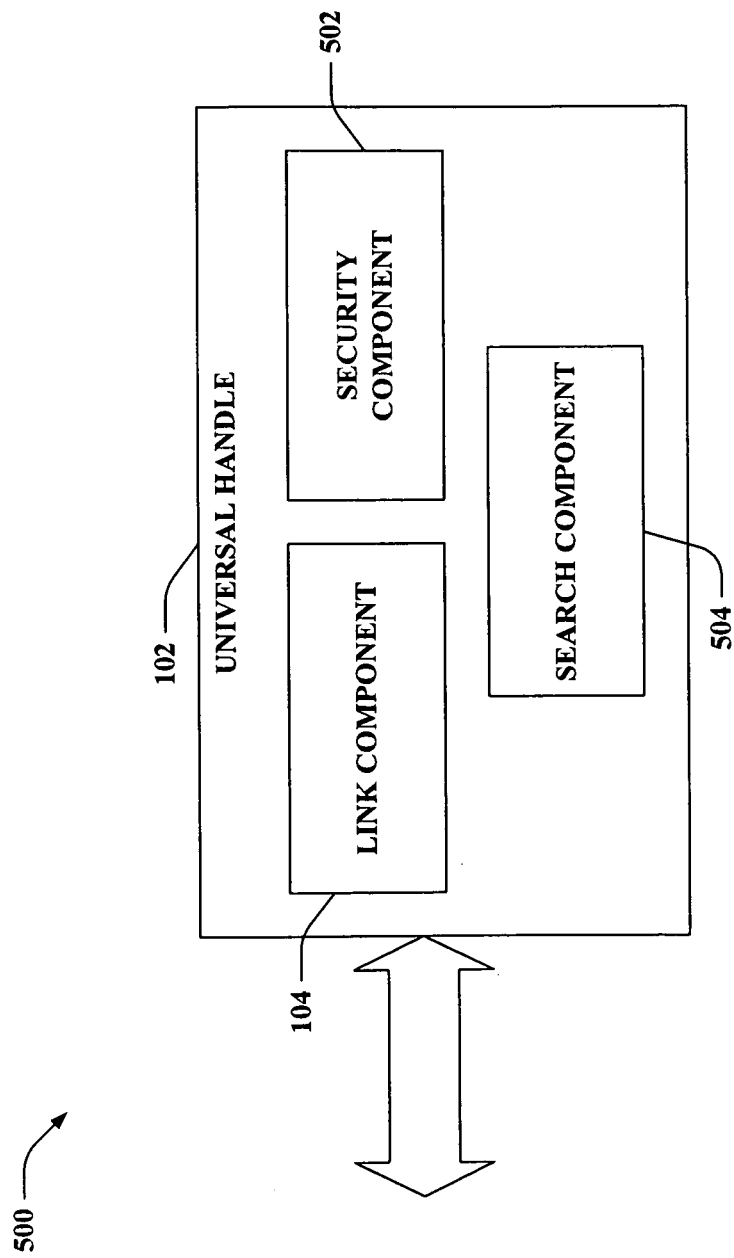
FIG. 5 illustrates a block diagram of an example system that provides security and enables searching with a universal handle.

Referring to FIG. 5, illustrated is an example system 500 that provides security and enables searching with a universal handle (e.g., the universal handle 102). The universal handle 102 includes the link component 104 for connecting to a network (e.g., Internet, intranet, WAN, WLAN, cellular network, . . . ); additionally, the link component 104 can enable connecting to a variety of devices, instruments, etc. as described herein. Further, the universal handle 102 can include a security component 502 and a search component 504.

The security component 502 can secure data retained in memory associated with the universal handle 102, data communicated to and/or from the universal handle 102, and so forth. Further, the security component 502 can authorize and/or authenticate users of the universal handle 102 (e.g., based upon biometrics, data retained in memory such as of a removable memory chip, credentials, . . . ). For instance, the security component 502 can limit access to a user's medical records. Pursuant to another illustration, the security component 502 can authorize and/or authenticate a user to mitigate insurance fraud. The security component 502 can also encrypt and/or decrypt data.

The search component 504 can utilize data obtained by the universal handle 102 to search, browse, etc. other data. For instance, the other data can be content retained on websites, information stored in databases (e.g., records, . . . ), and so forth. According to an illustration, the search component 504 can tailor a search and/or filter results from a search based upon data obtained, retained, evaluated, etc. by the universal handle 102. Moreover, the search component 504 can search for nearby, available individuals (e.g., experts, doctors, . . . ) capable to address a condition diagnosed by the universal handle 102.

According to an example, a consumer version of the universal handle 102 can be provided. The consumer version can provide functionality to enable a user (e.g., consumer) to check medical conditions. For instance, a parent can employ the universal handle 102 to view inside of her child's ear, measure her own temperature, check a pulse rate, photograph a rash, view inside her throat, listen to chest sounds (e.g., heart beat, breathing, . . . ), and so forth. Moreover, the universal handle 102 can communicate (e.g., via the link component 104 when in proximity) with home testing medical equipment that can be utilized by the patient (e.g., glucometer, . . . ) to gather medical related data. The universal handle 102 (e.g., the data analysis component 402 of FIG. 4) can be a intermediary to determine whether monitored conditions are or are not risk symptoms that should be addressed by a physician. Further, the search component 504 can search a directory, index, Internet, database, etc. based upon the captured data; for instance, the sources to be searched can be more focused rather than all content on the Internet (however, the claimed subject matter is not so limited). Pursuant to an illustration, the universal handle 102 can connect to a broadband connection, locate a physician (e.g., in real time) that is available at that moment in time, effectuate a search weighted according to the patient's medical record (e.g. search tailored to medical conditions of the patient, . . . ), and so forth. Moreover, the universal handle 102 can consider the user's (e.g., patient's) insurance plan, medical record (e.g., dynamic medical record, . . . ), and so forth when yielding such an output (e.g., physician referrals, search results, . . . ). Further, the consumer version of the universal handle 102 can be preloading with records, profiles, preferences, etc. of one or more patients and can be subscribed to a medical service provider that can be affiliated with a local pharmacy, a network of physicians, and so forth. Information obtained by the universal handle 102 can be sent back to the patient's insurance company (e.g. which can provide a billing stream for the insurance company and/or the medical service provider). Additionally, the universal handle 102 can track patient condition over time after receiving medical care, and a grade of the physician's care can be tracked post hoc, which can be utilized to guide a referral pattern by the medical service provider and/or insurance company. Moreover, medical care auditing can leverage information collected by the universal handle 102. It is to be appreciated, however, that the claimed subject matter is not limited to the consumer version of the universal handle 102.

By way of another example, the universal handle 102 can be programmed to look for specific outbreaks of disease. Hence, if a plurality of universal handles is deployed in a geographic region, accurate disease related data can be gathered. For instance, the universal handles can be designed to evaluate for presence of Ebola markers, etc.; further, the universal handles can report the analyzed data (e.g., to provide real time statistics). Thus, accurate data collection can be yielded upon deploying a critical mass of the universal handles. It is contemplated, however, that the claimed subject matter is not limited to this illustration.

Figure 6:
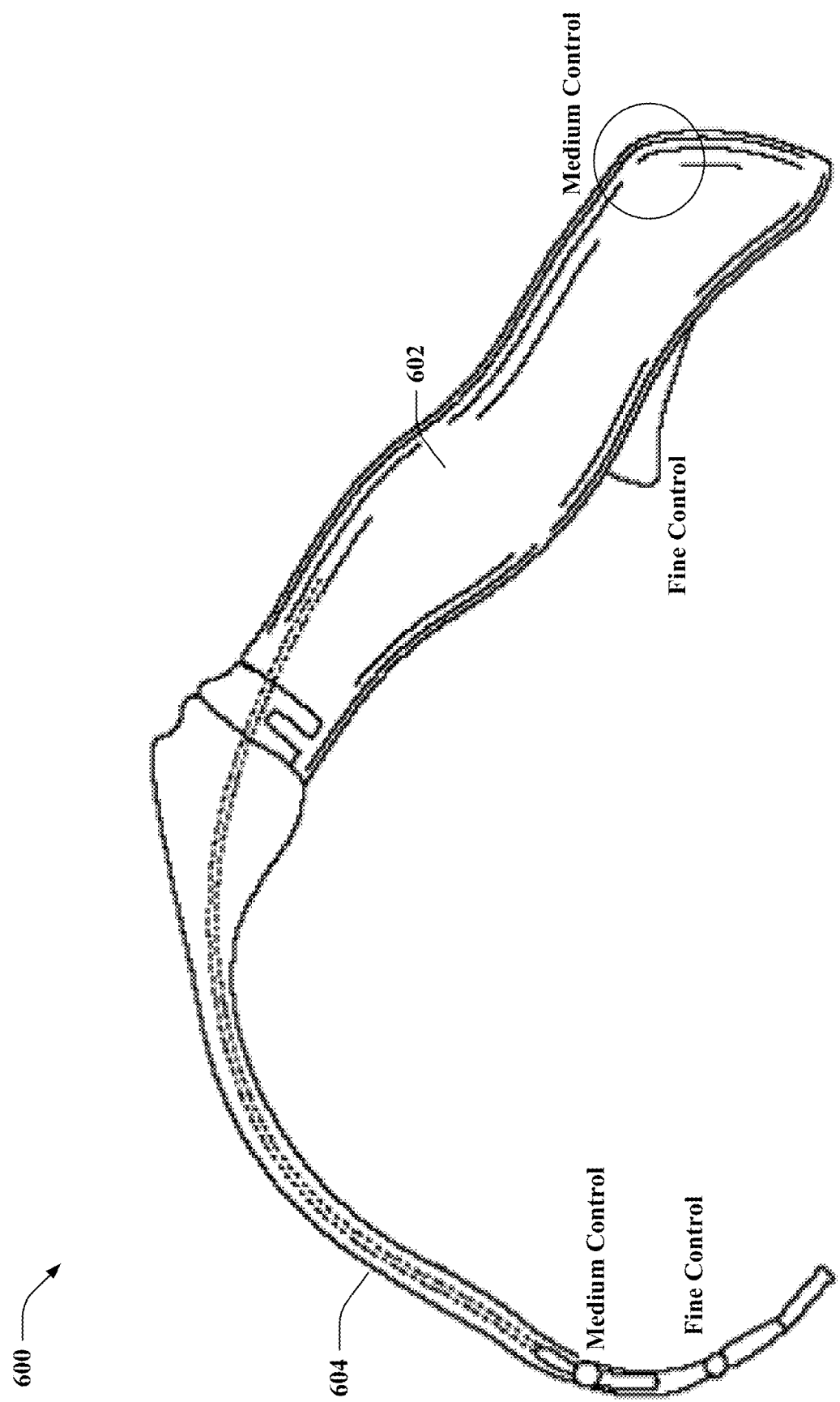
FIG. 6 illustrates an example schematic of an airway management apparatus in accordance with various aspects of the claimed subject matter.

Now turning to FIG. 6, illustrated is an example schematic of an airway management apparatus 600 in accordance with various aspects of the claimed subject matter. The airway management apparatus 600 can be a combination of the universal handle 102 and the managed external device 306 described herein. It is to be appreciated that the claimed subject matter is not limited to the depicted example schematic. The apparatus 600 can enable placement of an endotracheal tube during induction of general anesthesia and/or for emergency management of the airway during any type of respiratory embarrassment in a controlled operating room environment, other hospital location such as the emergency department, or outside the hospital in any number of field situations. For example, the apparatus 600 can include one or more cameras that can be maneuvered in close proximity to the opening of the trachea. By allowing maneuvering of the one or more cameras, a health care provider employing the apparatus 600 can have an increased chance of appropriately placing an endotracheal tube. Further, the apparatus 600 can provide direct, visual feedback that the endotracheal tube is in a proper place, and thus, mitigate adverse events associated with a misplaced tube.

The apparatus 600 can be a self-contained single piece. For instance, the apparatus 600 can include a handle 602 (e.g., the universal handle 102 of FIG. 1) and a blade 604 (one of the managed external devices 306-308 of FIG. 3). As such, the apparatus 600 can have similarity to a conventional Macintosh laryngoscope with notable variations as discuss below. According to another example, the blade 604 can be removable from the handle 602 of the apparatus 600 and/or replaceable (e.g., the blade 604 or a portion thereof can be disposable); however, the blade 604 need not be removable from the handle 602 and/or replaceable. It is contemplated that blades of various sizes, shapes, thicknesses, material compositions, etc. can be attached to a common handle, for instance. According to another illustration, it is to be appreciated that the handle 602 can be a universal handle (e.g., the universal handle 102 of FIG. 1); as such, the handle 602 can interchangeably connect with the blade 604 and/or any disparate type of device (e.g., bronchoscope, ENT Dido scope, . . . ) while providing similar functionality (e.g. power source, wireless communication, data storage, . . . ) as described below to each of these disparate types of devices. Such a universal handle 602 can be portable. Further, the universal handle 602 can include servo-control capabilities that can effectuate operating substantially any type of device to which the handle 602 is attached. Moreover, the universal handle 602 can enable acquisition, archiving, transmission (e.g., wireless, wired, . . . ), generation of reports, etc. related to data associated with the attached device (e.g., the blade 604, bronchoscope, ENT Dido scope, mediastinoscope, colonoscope, . . . ) as described below. For example, data can be obtained via the device attached to the universal handle 602 by way of fiberoptics, cameras, ultrasound, and/or substantially any type of sensor(s).

The blade 604 can be a dynamically articulating laryngoscope blade that can be controlled to configure to normal anatomic variants as well as pathologic abnormalities to facilitate placing an endotracheal tube into the trachea. Thus, the blade 604 can accommodate variation in normal and abnormal anatomy of the upper airway resulting in less airway trauma and stimulation stress on a patient undergoing intubation. In contrast to conventional blades that commonly have fixed curvature, the blade 604 can be controlled via the handle 602 to adjust the curvature, manipulate portions or the entire blade 604 relative to the handle 602, etc. Accordingly, the apparatus 600 can be slid along the handle 602 to lengthen or shorten the blade. Further, upon obtaining the proper blade length, the blade 604 can be flexed up or down via a medium control to provide a crude view of the vocal cords (e.g., camera(s) can be positioned nearby the medium control articulation point). Additionally, a tip of the blade 604 can be manipulated via a fine control to alter the position of a patient's epiglottis to provide a clearer view of the vocal cords. It is contemplated that the blade 604 can be manipulated at any disparate location(s) upon the blade 604 other than or in addition to those depicted in the illustrated schematic.

The blade 604 can also have one or more digital cameras (e.g., stereoscopic cameras) mounted thereupon. The digital camera(s) can be moved independently of the blade 604, for instance, to allow for optimal viewing of the laryngeal opening. Further, articulation of the blade 604 can enable positioning the camera(s) such that an unobstructed view of the vocal cords can be obtained. It is to be appreciated that the camera(s) can be integrated into the blade 604, attached to the blade 604 (e.g., permanently, temporarily, . . . ), and so forth. According to an example, the camera(s) can be removeably connected to the blade 604 thereby allowing for replacement.

The handle 602 can include a power supply. For instance, the power supply can be a battery (e.g., a lithium-battery). Additionally, the handle 602 can comprise an interface that enables connecting to a cradle. When connected to (e.g., docked upon) the cradle, the power supply can be recharged, digital images and/or video obtained by the one or more digital cameras can be transferred, and so forth. In addition, the apparatus 600 (e.g., the handle 602) can include an integrated processor. By way of illustration, the processor can control operation associated with the one or more digital cameras; thus, the processor can enable capturing digital images and/or video with the camera(s) and/or transferring the captured data to a remote location (e.g., via the interface when connected to the cradle, a wireless connection, . . . ).

The handle 602 can also include controls that allow for manipulation of the articulating blade 604. The differing controls can provide varying precision of manipulation (e.g., medium control, fine control, . . . ). By way of illustration, the controls included with the handle 602 can mechanically alter the size, shape, curvature, orientation, etc. of the blade 604. Additionally or alternatively, the controls can transmit a signal that can initiate such alterations (e.g. employing a servo motor). Also, the handle 602 can comprise a control that releases the integrated channel for passage of the endotracheal tube or other airway device.

The attached blade 604 can be constructed of a plurality of flat metal blades that articulate on one another allowing for the blade 604 to dynamically assume multiple configurations depending on the patient's airway anatomy. Thus, the blade 604 can include multiple articulating plates that allow the blade 604 to flex throughout its length as well as at the tip. The control apparatus for this manipulation can be positioned within the handle 602.

The apparatus 600 can provide a number of advantages as compared to conventional devices. Every patient has a different anatomically structured airway and securing an airway can be difficult. The apparatus 600 can mitigate such difficulty by producing a reasonable view of the tracheal inlet thereby allowing for placement of an endotracheal tube. Additionally, the curvature of the laryngoscopic blade 604 can change in real time while in the oral cavity via the controls to accommodate for normal variations in airway anatomy or pathologic airway conditions (e.g., tumors). By allowing for variation in the curvature of the blade 604 while within the oral cavity, changing the blade 604 to provide for variations in size and/or shape need not occur (e.g. reducing intubation time, . . . ). Further, trauma to the upper airway can be reduced by employing the apparatus 600 and the physiologic stress on the patient associated with applying force on the tongue and oral cavity tissues can be lessened through a more efficient utilization of force and viewing angles. Moreover, the ability to visualize the vocal cords is often obstructed by the epiglottis covering the tracheal opening when employing conventional devices. In order to effectively overcome this obstacle, one can place the laryngoscope blade under the epiglottis to bring it out of the way or anteriorly displace the epiglottis by applying anteriorly directed force in the velecula, elevating the epiglottis with the adjoining soft tissue. Traditional laryngoscopes oftentimes fail to do this since to apply anterior force in the velecula requires the operator to "hinge" back on the blade, driving the proximal end of the blade into the patient's incisors. This can result in injury to the teeth, oral mucosa, or cause trauma to the lower part of the airway with adequately improving the view of the tracheal opening. In contrast, the portion of the blade 604 associated with fine control (e.g. tip of the blade 604) can pull the epiglottis out of the way to allow for viewing the vocal cords.

In addition to difficulty associated with visualization of the laryngeal aperture, once the anesthesia provider obtains a view, it is sometimes difficult to maneuver the endotracheal tube into the trachea to complete the process of securing an airway while employing conventional techniques. The apparatus 600 can mitigate the maneuvering related difficulty by having a channel positioned along the side of the blade 604 that can include a ball bearing and spring-loaded pusher plate to dynamically adapt to variously size endotracheal tubes or airway intubation stylets. The channel can be positioned and/or adapt its position as the blade 604 articulates to deliver the tip of the endotracheal tube to the center of the camera viewing apparatus. This allows the operator to center the laryngeal aperture and watch under direct vision as the endotracheal tube passes into the trachea.

Moreover, in certain situations, patients may present with a physical exam that deems them as very challenging airways because of anatomic changes or pathologic tumors. In these situations, patients may need to have their airways secured without the addition of any anesthetic medications that may lead to sedation and a cessation of breathing or an obstruction of the patent airway that they initially presented with making things more urgent and often more difficult and stressful on the patient. Applying local anesthetics to these specific airways allows for the anesthesiologist to place a fiberoptic camera or gently place a laryngoscope to determine if it is safe to place the patient asleep prior to placing a breathing tube. The apparatus 600 can have a channel that operates using Bernoulli principles to atomize liquid local anesthetic medications. This coupled with the camera system can allow one to completely topicallize the airway while the device is being placed resulting in a much more comfortable state of the patient as well as maintaining a spontaneously breathing state.

According to another example, a sleeve-type cover can be placed over the blade 604 and/or the handle 602 to enable reuse of the device without cleaning. According to an illustration, the sleeve-type cover can be disposable; however, it is to be appreciated that the cover can be sterilized to allow for reuse of the cover. Moreover, the cover can allow for the blade 604 to be articulated as well as data to be collected (e.g., via the cameras attached to the blade 604, . . . ) while mitigating obstruction thereof.

Figure 7:
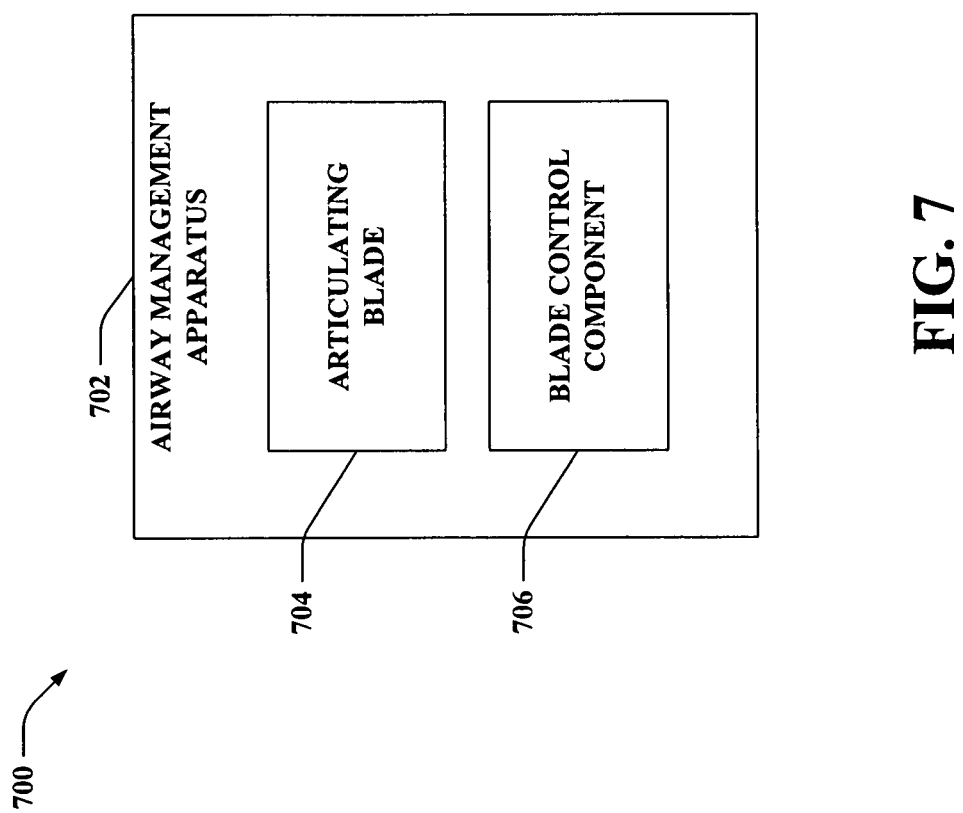
FIG. 7 illustrates a block diagram of an exemplary system that facilitates intubating a patient.

Turning to FIG. 7, illustrated is an example system 700 that facilitates intubating a patient. The system 700 includes an airway management apparatus 702 (e.g., the apparatus 600 of FIG. 6) that enables performing direct laryngoscopy. The airway management apparatus 702 further includes an articulating blade 704 (e.g. the blade 604 of FIG. 6, one of the managed external devices 306-308 of FIG. 3, . . . ) and a blade control component 706 (e.g., included in the handle 602 of FIG. 6, the universal handle 102 of FIG. 1, . . . ).

The articulating blade 704 can be manipulated in any manner. For instance, the size, length, shape, curvature, and the like of the articulating blade 704 or portion(s) thereof can be changed. By way of example, in contrast to some conventional devices with blades that have a fixed curvature, the curvature of the articulating blade 704 can be altered based upon anatomic characteristics of a patient. Further, such adjustments can be effectuated while positioning the airway management apparatus 702 proximate to the trachea within the oral cavity (e.g., as opposed to altering these features while the apparatus is removed from the patient's mouth and thereafter positioning the apparatus). The articulating blade 704 can accommodate variation in normal and abnormal anatomy of the upper airway. Moreover, the articulating blade 704 can reduce airway trauma and stimulation stress on the patient undergoing intubation. Additionally, the articulating blade 704 can be thinner than conventional blades employed in connection with typical laryngoscopic devices.

The articulating blade 704 can have any number of articulation points that can allow for varying degrees of control. For instance, a first articulation point can allow for crudely obtaining a view of the vocal cords (e.g. by adjusting an angle of camera(s) to be directed at the vocal cords from the base of the tongue). Further, a second articulation point can improve the crude view by manipulating the epiglottis of the patient.

The blade control component 706 can enable manipulating the articulating blade 704. The blade control component 706 can be included in a handle (e.g., the handle 602) of the airway management apparatus 702. The blade control component 706 can obtain substantially any type of input to yield a corresponding alteration of the articulating blade 704. For example, the blade control component 706 can receive an input from a user of the airway management apparatus 702 (e.g., via a button, joystick, switch, lever, touch screen, voice command, sensor, mouse, trigger, . . . ). According to another illustration, an input can be provided from a remotely located user via a signal; thus, telemedicine can be performed such that a user other than a user physically touching the airway management apparatus 702 can provide input utilized to manipulate the articulating blade 704. Moreover, the blade control component 706 can adjust the articulating blade 702 mechanically, via an electrical signal, and so forth. By way of illustration, the input can be utilized to control one or more motors to manipulate the articulating blade 702. For instance, servo motor(s) can leverage the input to smoothly control movement of the articulating blade 702 in substantially any number of planes. Additionally or alternatively, linear motor(s) can employ the input to manipulate the articulating blade 702. Thus, according to an example, the blade control component 706 can receive a user input, which can control servo motor(s) and/or linear motor(s) that can elongate, shorten, alter elevation, etc. associated with the articulating blade 704 or a portion thereof.

The articulating blade 704 can further include an adaptable channel (not shown). The adaptable channel can be adjusted in a size, shape, etc. (e.g., while the airway management apparatus 702 is being employed upon a patient). Also, the adaptable channel can allow for secure and directional placement of variously sized endotracheal tubes, intubating stylets, jet ventilation equipment, and the like. The adaptable channel can be employed to facilitate passing an endotracheal tube into the trachea under direct vision, for example.

The articulating blade 704 can also include a light transmission component (not shown) that can illuminate a patient's airway. For instance, controls (e.g., that alter on/off state, intensity, direction, wavelength, . . . ) for the light transmission component can be included in the handle of the airway management apparatus 702. Moreover, the light transmission component can be permanently affixed to, incorporated into, temporarily attached to (e.g., removable, replaceable, . . . ), etc. the articulating blade 704. Further, the articulating blade 704 can comprise an airway atomizing device, which can be used to deliver topical anesthesia during placement of an endotracheal tube.

Figure 8:
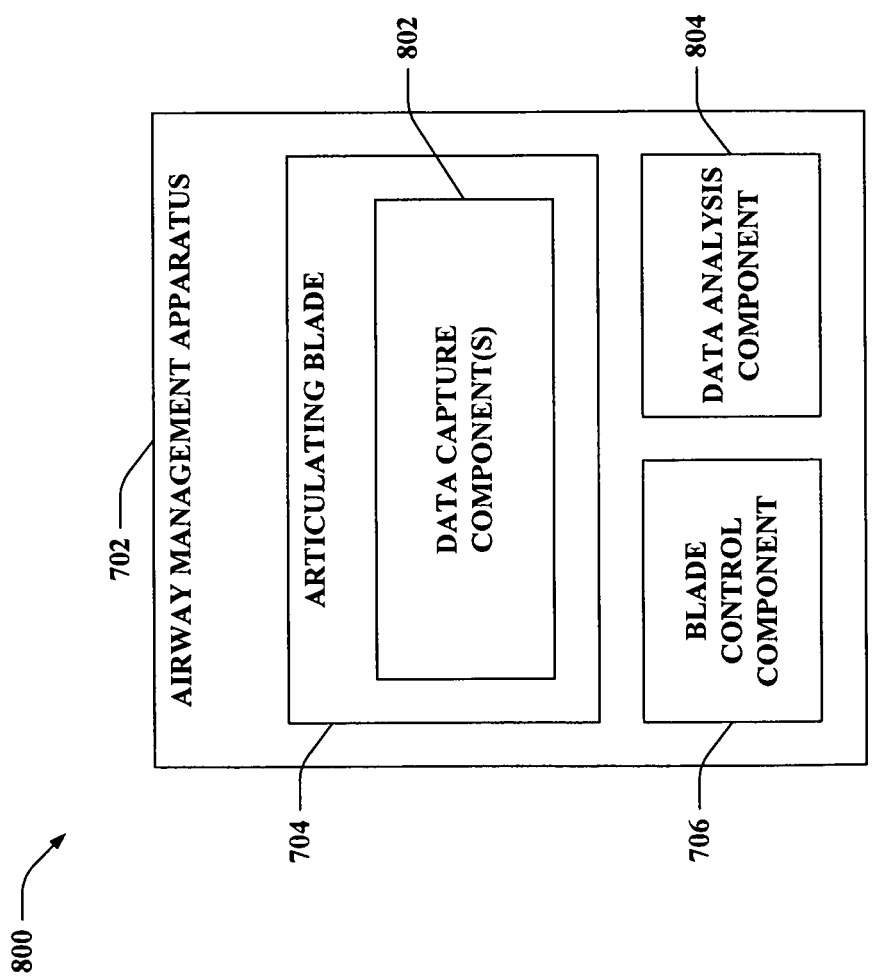
FIG. 8 illustrates a block diagram of an exemplary system that enables performing video laryngoscopy in accordance with various aspects.

Now turning to FIG. 8, illustrated is an example system 800 that enables performing video laryngoscopy in accordance with various aspects. The system 800 includes the airway management apparatus 702, which can further comprise the articulating blade 704 and the blade control component 706. The articulating blade 704 can also include data capture component(s) 802 that collect substantially any type of data (e.g., visual, audio, chemical, pressure, temperature, . . . ). It is contemplated that any number and/or type of data capture component(s) 802 can be utilized in connection with the airway management apparatus 702. A data analysis component 804 (e.g., data analysis component 402 of FIG. 4) can further employ (e.g., aggregate, evaluate, . . . ) the data obtained by the data capture component(s) 802.

According to an example, the data capture component(s) 802 can be a plurality of cameras (e.g., two, more than two, . . . ) that can provide a stereoscopic view. The cameras can be located upon the articulating blade 704 at an articulation point that can be positioned at the base of the tongue looking up when the apparatus 702 is utilized upon a patient. Thus, as opposed to conventional techniques where the vocal cords are viewed from outside of the mouth, the cameras can capture a view from the base of the tongue. The cameras can be any type of digital cameras including, for instance, charge coupled devices (CCDs) or CMOS sensors that can capture images. The data analysis component 804 can utilize the data obtained by these cameras to generate an image with depth perception that allows for focusing at various depths. The data analysis component 804 can enable stereoscopic visualization of the laryngeal aperture allowing for depth perception to improve endotracheal tube placement success. The data analysis component 804 can combine two or more images to create a composite image with depth (e.g., three dimensional), for example. Further, the data analysis component 804 can yield an output that can be transmitted, displayed, stored, matched to a pattern, etc.

It is contemplated that the data capture component(s) 802 can include any number of digital cameras. The digital camera(s) can be mounted on the articulating blade 704 and moved independently of the blade 704 allowing for improved viewing of the laryngeal opening. These cameras can collect video data and/or still image data. Further, it is contemplated that the cameras can switch between collecting video and still images, simultaneously collect video and still images, or statically collect a particular type of data. Moreover, the cameras can be high definition cameras, for example. Further, the cameras can include a heating element (e.g., coil, light emitting diode, . . . ) to mitigate fogging while positioned within the oral cavity.

The data analysis component 804 can assemble data from the data capture component(s) 802. For example, a plurality of data capture component(s) 802 can provide input data to the data analysis component 804, which can thereafter aggregate such input data to yield a unified output. According to another illustration, the data analysis component 804 can perform pattern recognition upon the data from the data capture component(s) 802 to identify whether an endotracheal tube is properly positioned, misplaced, and so forth. Further to this illustration, an indication (e.g., alarm) of the recognized state can be yielded.

According to another example, the data capture component(s) 802 can be substantially any type of sensor and/or an interface that can connect with an externally located sensor. For instance, gaseous properties (e.g., carbon dioxide levels, . . . ) can be tracked by such sensors to provide feedback associated with placement of an endotracheal tube in the esophagus of a patient; thus, the monitored carbon dioxide level can be compared to a threshold (e.g., 2-3%, substantially any other percentage of carbon dioxide, . . . ) and, if the monitored level is below the threshold, the endotracheal tube can be determined to be positioned in the esophagus. Further, any other type of property (e.g., pH level, humidity, . . . ) can be monitored by these sensors to yield similar types of feedback. Moreover, the feedback can be evaluated by the data analysis component 804 to generate an associated output.

Figure 9:
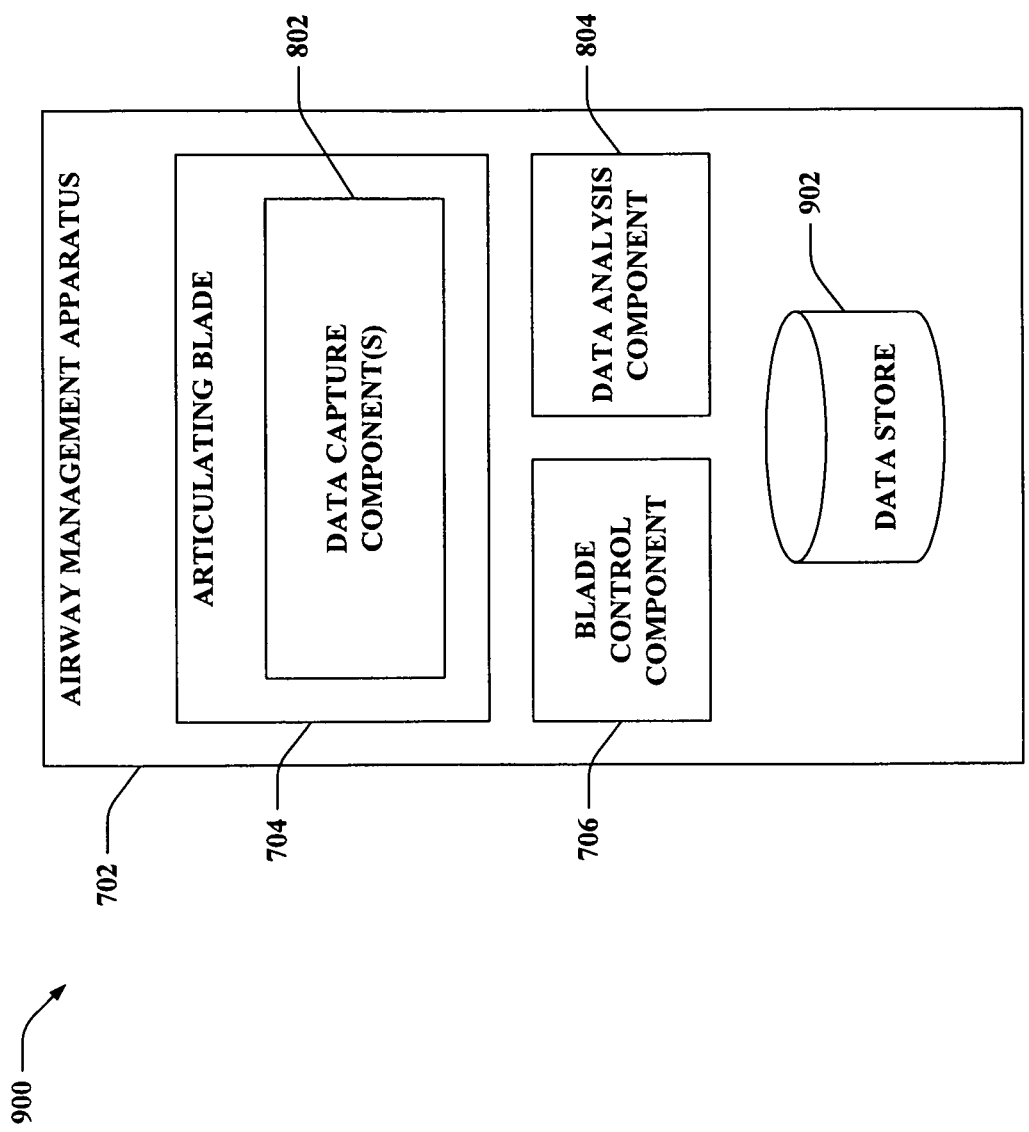
FIG. 9 illustrates a block diagram of an exemplary system that enables storing recorded data.

With reference to FIG. 9, illustrated is an example system 900 that enables storing recorded data. The system 900 includes the airway management apparatus 702, which can further comprise the articulating blade 704, the blade control component 706, and the data analysis component 804. Additionally, the articulating blade 704 can include the data capture component(s) 802. The airway management apparatus 702 can also include a data store 902 (e.g. the data store 404 of FIG. 4) that can retain the data obtained by the data capture component(s) 802 and/or evaluated by the data analysis component 804.

The data store 902 can be, for example, either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable programmable ROM (EEPROM), or flash memory. Volatile memory can include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM). The data store 902 of the subject systems and methods is intended to comprise, without being limited to, these and any other suitable types of memory. In addition, it is to be appreciated that the data store 902 can be a server, a database, a hard drive, and the like.

By way of example, the data store 902 can be utilized to document difficult intubations. Thus, data such as images, video, alarms, and the like concerning such intubations can be retained in the data store 902. Accordingly, the data store 902 can be a flash memory chip that can be removed from the airway management apparatus 702 (e.g., from the handle) and placed in a patient's file. Additionally or alternatively, upon the airway management apparatus 702 being placed in a cradle, data retained in the data store 902 can be archived to hospital records (e.g., upon a server), printed in a report, etc. Further, the data can be archived via a wireless connection to such server. The data can be archived automatically, periodically, in response to a received request, and so forth. Further, it is contemplated that the data store 902 can similarly be included in any other type of medical device in addition to the airway management apparatus 702 to enable documenting procedures performed upon patients with these other types of medical devices.

Figure 10:
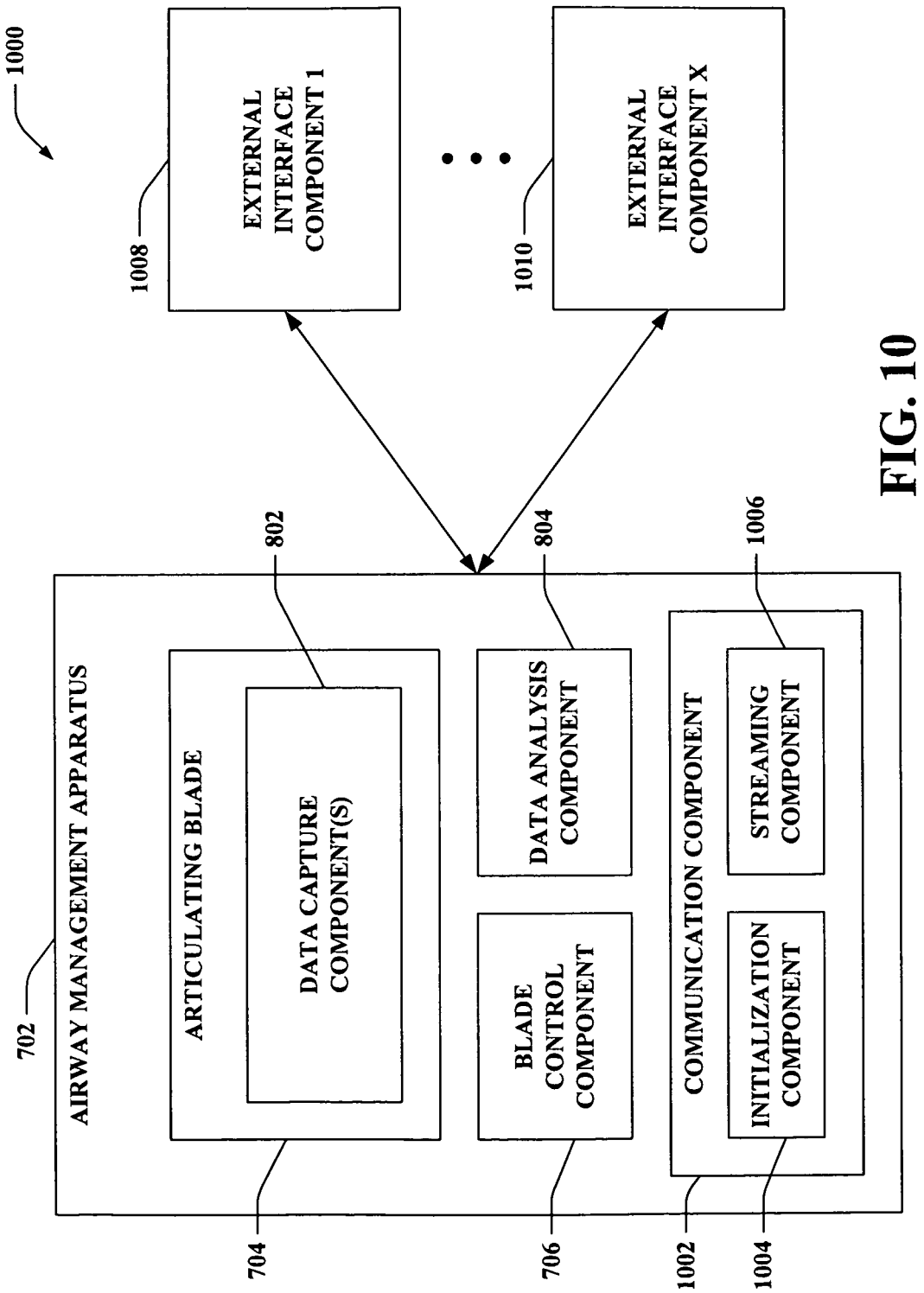
FIG. 10 illustrates a block diagram of an exemplary system that enables wirelessly transferring data captured from a laryngoscope.

Referring now to FIG. 10, illustrated is an example system 1000 that enables wirelessly transferring data captured from a laryngoscope. The system 1000 includes the airway management apparatus 702, which further comprises the articulating blade 704 (e.g., that further includes data capture component(s) 802), the blade control component 706, and data analysis component 804 as described above. The airway management apparatus 702 can also include a communication component 1002 (e.g., the link component 104 of FIG. 1) that can transmit and/or receive data within the system 1000. The communication component 1002 can further include an initialization component 1004 (e.g. configuration component 304 of FIG. 3) and a streaming component 1006. Moreover, the communication component 1002 can enable the airway management apparatus 702 to communicate with one or more external interface components (e.g., an external interface component 1 1008, . . . , an external interface component X 1010, where X can be any integer).

The external interface components 1008-1010 can be, for example, cellular phones, smart phones, laptops, handheld communication devices, handheld computing devices, satellite radios, global positioning systems, personal digital assistants (PDAs), and/or any other suitable device. Additionally, the external interface components 1008-1010 can be any type of device with a monitor. The external interface components 1008-1010 can be located within proximity of the airway management apparatus 702. According to another example, one or more of the external interface components 1008-1010 can be positioned outside of a local vicinity of the airway management apparatus 702.

The initialization component 1004 can determine whether any external interface components 1008-1010 are within range. Thus, a list of identities of these external interface components 1008-1010 can be populated by the initialization component 1004. Thereafter, one or more of the listed external interface components 1008-1010 can be selected and data from the data analysis component 804 can be transmitted to the selected external interface component(s) 1008-1010 (e.g., which can thereafter output the data). For instance, the external interface component(s) 1008-1010 can visually display the output, yield audio output, and so forth.

Additionally, the initialization component 1004 can allow for connecting to remotely located external interface components 1008-1010. For instance, the communication component 1002 can enable communicating from the airway management apparatus 702 over an infrastructure based network (e.g. cellular network). Thus, a specially trained individual located anywhere in the world can be presented with feedback from the data capture component(s) 802. Further, this individual can control manipulation of the articulating blade 704 and/or the data capture component(s) 802 from the remote location.

By way of illustration, a monitor can be positioned in an operating room in which the airway management apparatus 702 is being employed. The initialization component 1004 can identify that the monitor is within proximity and set up transfer of data to the monitor. For example, the monitor can automatically be initialized by the initialization component 1004; thus, upon moving within range of the monitor, transmission can occur between the communication component 1002 and the monitor to enable display upon the monitor of data collected by the airway management apparatus 702. Additionally or alternatively, the initialization component 1004 can create a list of available devices (e.g., external interface components 1008-1010) including the monitor, and a selection may be made based upon a user input, a preference, a ranking, security levels, etc.

The streaming component 1006 can enable real-time transfer of data from the data analysis component 804 to one or more of the external interface components 1008-1010. Thus, the streaming component 1006 can allow for an image obtained with the data capture component(s) 802 from a patient's oral cavity to be displayed upon a PDA or any other external interface component 1008-1010 in real-time as the apparatus 702 is manipulated within the oral cavity. Further, the streaming component 1006 can allow for the data to be transmitted to a disparate device for storage (e.g. a remotely located data store).

The communication component 1002 can utilize any type of wireless technology to transfer data (e.g., WiFi, 802.11b, g, n, Bluetooth, . . . ). Thus, the communication component 1002 can enable wireless digital transmission of digital images to allow for remote viewing of airway manipulation, digital recording of procedures, porting images to video equipment in place such as anesthesiology monitoring or portable handle communication devices, and so forth. Moreover, the communication component 1002 can receive feedback from one or more of the external interface components 1008-1010; such feedback can control manipulation of the articulating blade 704 by providing a signal to the blade control component 706, for example. Also, the feedback obtained by the communication component 1002 can enable moving the data capture component(s) 802 (e.g., shifting the view being captured). Accordingly, this type of feedback can enable performing telemedicine.

The system 1000 can further include an intelligent component (not shown) that can be employed by the airway management apparatus 702. For example, the intelligent component can infer which external interface component 1008-1010 within proximity to display data upon. Pursuant to another example, the intelligent component can infer potential errors in use associated with the airway management apparatus 702 (e.g., misplaced endotracheal tube, . . . ) and yield a corresponding alarm.

It is to be understood that the intelligent component can provide for reasoning about or infer states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g. support vector machines, neural networks, expert systems, Bayesian belief networks, fuzzy logic, data fusion engines . . . ) can be employed in connection with performing automatic and/or inferred action in connection with the claimed subject matter.

A classifier is a function that maps an input attribute vector, $x=(x1, x2, x3, x4, xn)$, to a confidence that the input belongs to a class, that is, $f(x)=confidence(class)$. Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hypersurface in the space of possible inputs, which hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

Figure 11:
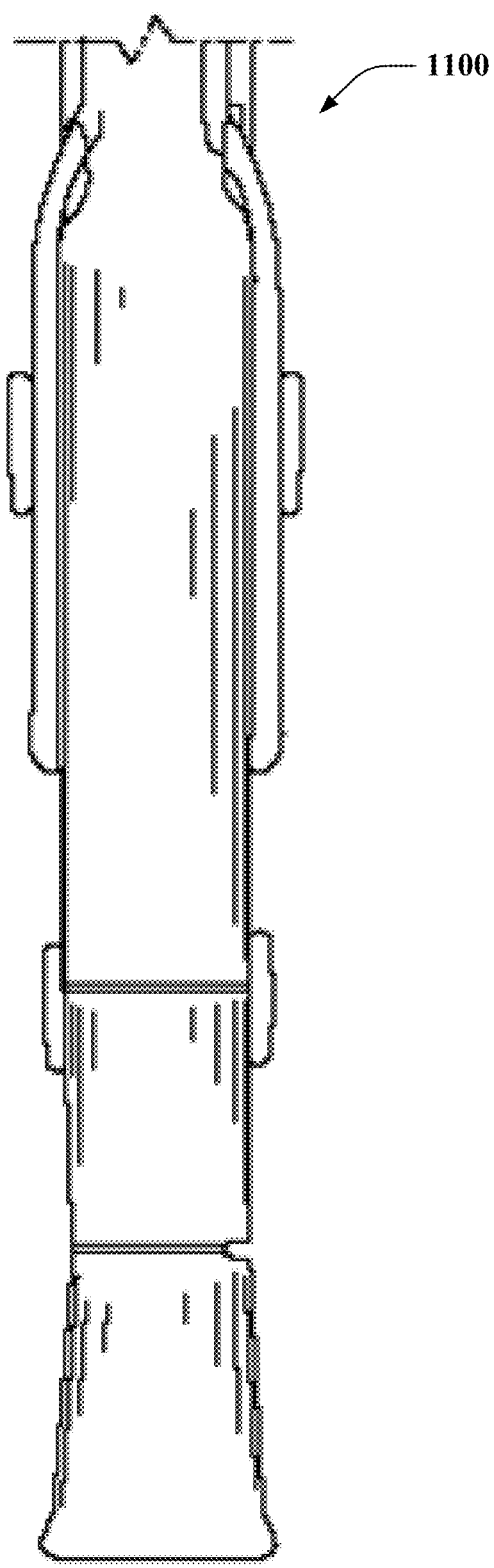
FIG. 11 illustrates another example schematic of an airway management apparatus in accordance with various aspects of the claimed subject matter.
Figure 12:
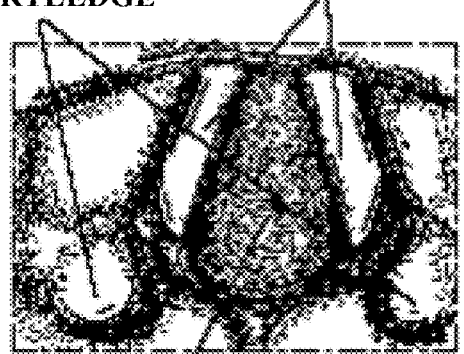
FIGS. 12 and 13 illustrate the vocal cords and laryngeal aperture.
Figure 13:
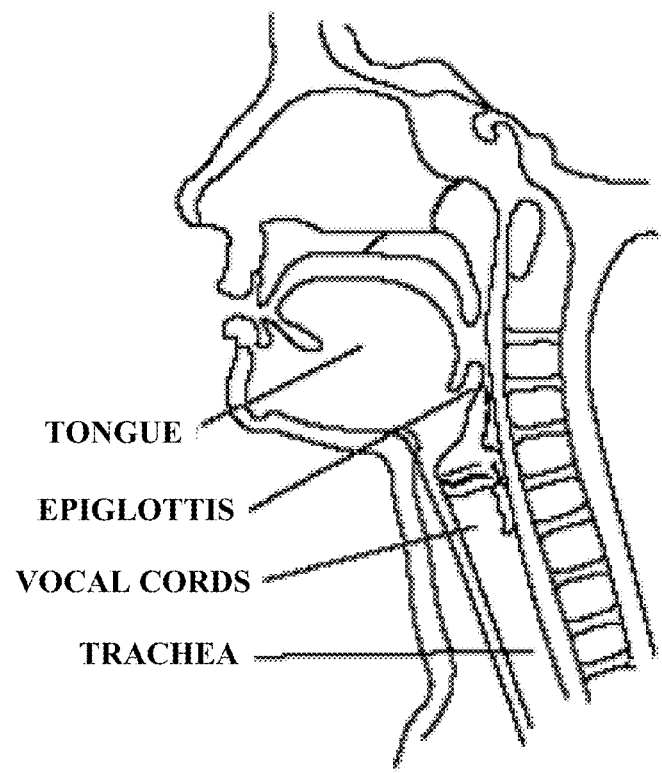
Figure 14:
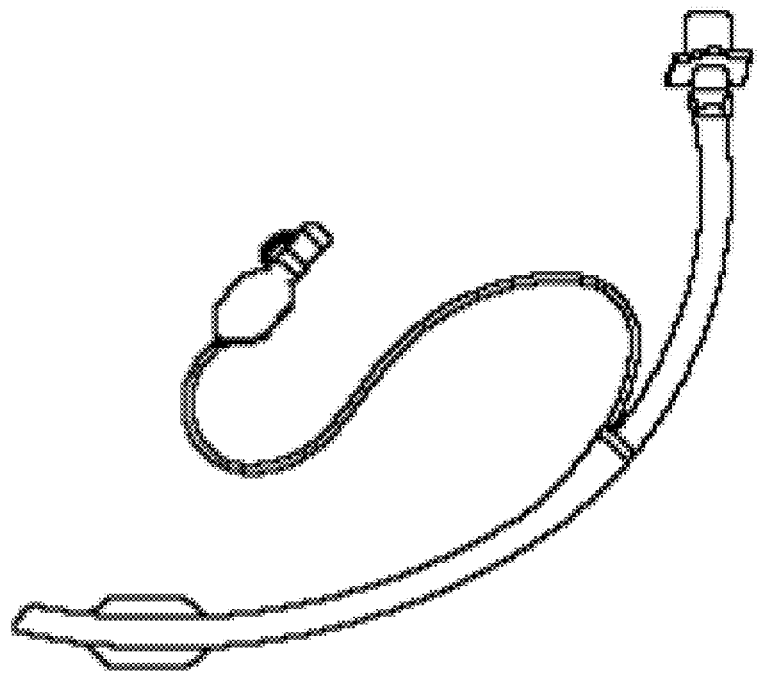
FIG. 14 illustrates an example endotracheal tube that can be utilized in connection with the airway management apparatus described herein.
Figure 15:
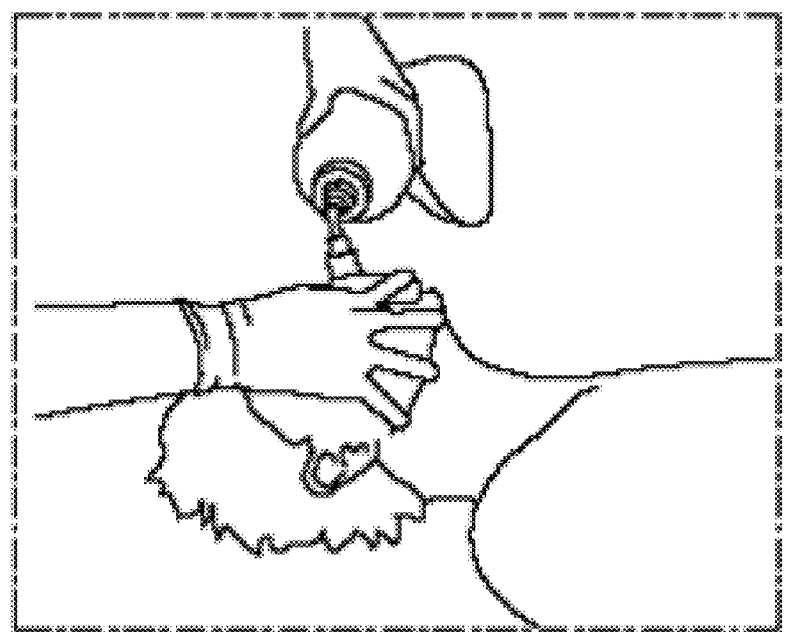
FIG. 15 illustrates bag-mask ventilation.

Referring to FIG. 11, illustrated is another example schematic of an airway management apparatus 1100. The schematic shown in FIG. 11 is a top view of the schematic depicted in FIG. 1. FIGS. 12 and 13 depict the vocal cords and laryngeal aperture. FIG. 14 illustrates an example endotracheal tube that can be utilized in connection with the airway management apparatus described herein. FIG. 15 illustrates bag-mask ventilation.

A typical example operating room intubation scenario proceeds as follows. A patient who is spontaneously breathing on their own is placed in a supine position and supplemental oxygen is provided in an attempt to "fill" their lungs, blood, and tissues with higher than normal oxygen levels, hyperoxygenation. This is done to prevent a fall in oxygen levels, deaturation or the oxygen carrying molecules hemoglobin in the blood, during the period when the patient is not breathing as a result of the administration of anesthetic drugs that render patients unconscious and apneic (not breathing on their own) and the initiation of mechanical ventilation through the properly placed endotracheal tube. Typically, with hyperoxygenation, an anesthesiologist has about 2-3 minutes to place the endotracheal tube into the trachea before the patient becomes hypoxic requiring the addition of supplemental oxygen delivered with bag-mask ventilation (as shown in FIG. 15). In certain situations, a failure to place the endotracheal tube into the trachea and start mechanical ventilation, bag-mask ventilation is extremely difficult or not possible resulting in severe hypoxia and potentially death or irreversible brain damage. These delays in securing an airway with the proper placement of an endotracheal tube extend the amount and time of anesthesia and add potential physiologic derangements that are poorly tolerated in certain patient populations, especially the elderly.

Complications with placement of an endotracheal tube do not end with visualization of the opening to the trachea. Placement of a rigid laryngoscope into someone's mouth and using this to forcefully move the tongue, lower jaw, and upper airway soft tissue out of the way is very stimulation and not reliably blunted with standard anesthetic induction medications. Endotracheal intubation can result in severe physiologic stresses in patient's that often lead to increases in heart rate and blood pressure in the adult population, and a precipitous fall in heart rate in pediatric patients. These stresses are not well tolerated in certain patient groups with co-existing heart conditions or those already at physiologic extremes (such as trauma patients).

If one starts with a patient who is spontaneously breathing and oxygenating themselves, which pertains to the majority of patients taken to the operating room for elective procedures, it is assumed they will be amenable to the placement of an endotracheal tube once anesthesia is administered, provided a comprehensive airway evaluation does not uncover any potential problems. Once anesthesia is administered, a once patent airway can become compromised by a relaxation of the upper airway musculature resulting in an obstruction that can be very difficult to overcome with bag-mask ventilation or the use of other airway devices. In these patients, a once patent airway when they were awake can now require immediate placement of an endotracheal tube into a trachea that is remote to the anesthesiologist. As described herein, the development of endoscopic equipment including small, high resolution cameras and the ability to digitalize and transmit an image has the potential to improve the viewing of the laryngeal aperture resulting in an easier, quicker, less traumatic and with reduced physiologic perturbations in patients undergoing general anesthetic as well as those requiring intubation for some other emergency medical condition elsewhere inside or outside the hospital. To date, typical devices have been unable to overcome the problems encountered in conventional laryngoscopy and intubation.

Various types of endoscopic equipment are routinely being used in many areas of medicine and surgery. These devices can be ridged or flexible and typically consist of a system to deliver a high intensity light beam to the area to be visualized. This light delivery is usually in the form of a fiberoptic cable. Most of these devices also use an external cable to connect the endoscopic device to some external power/light generating source by an additional cable. The camera at the tip of the endoscopic device can consist of a CCD (charge coupled device) sensor, in the form of a light sensitive chip that converts an optical source into an electrical one, or an array of fiberoptic cables coherently aligned to deliver the light encoded image back to some video display system through an external cable connection.

The ubiquitous use of endoscopic equipment in the health care system today has resulted in some sophisticated equipment; however, the series of interconnected cables makes these devices difficult to maneuver in the best situations, severely complicating and emergency situation or a procedure performed outside a well controlled environment. In addition, the fragility of fiberoptic bundles results in frequent and easy damage of these cables adding to the escalating health care costs. Relatively minimal damage to the fiberoptic bundles leads to a degradation in image quality that is unusable for the delicate medical procedures the endoscope was designed for.

In light of all of these problems, it is desirable to provide a video laryngoscopic system that is easy to use, adaptable to the wide variation in normal and abnormal upper airway pathology we see every day in the hospital, facilitates easy placement into a patients oral cavity with little or no stimulation, and allows for the transmission of a digital image to any number of video monitoring systems using wireless technology in place of external cable connections.

The ability to easily articulate a laryngoscopic blade that has already been placed into someone's oral cavity allows for utilizing a single device across a wide spectrum of normal and abnormal anatomic situations. Coupled with an articulating blade, a coherently adapting channel to guide the endotracheal tube to the exact position where the camera is looking is required to place the endotracheal tube and not just visualize where it needs to go.

In certain airway situations, the placement of an endotracheal can only safely be accomplished by keeping a patient in an awake state and spontaneously breathing. In these situations, is it of paramount importance that one is able to adequately anesthetize the upper airway to blunt the cough reflex as well as to blunt any painful stimuli these patients would experience with the placement of the intubation equipment. A single airway device that takes all of these situations into account would decrease the time required for intubation, decrease the stress on the patient, and reduce the cost of equipment as well as equipment processing time and expense.

The aforementioned objectives can be achieved with a completely redesigned laryngoscopic blade, an integrated digital stereoscopic camera and high intensity, low power light source and light conducting system, the addition of a liquid, atomizing device for the delivery of local anesthetic or humidification to the airway mucosa, a specialized, dynamically sizing channel that adapts to the contour of the laryngoscopic blade allowing for the delivery of an endotracheal tube or other airway device to the exact position of the camera view.

Figure 16:
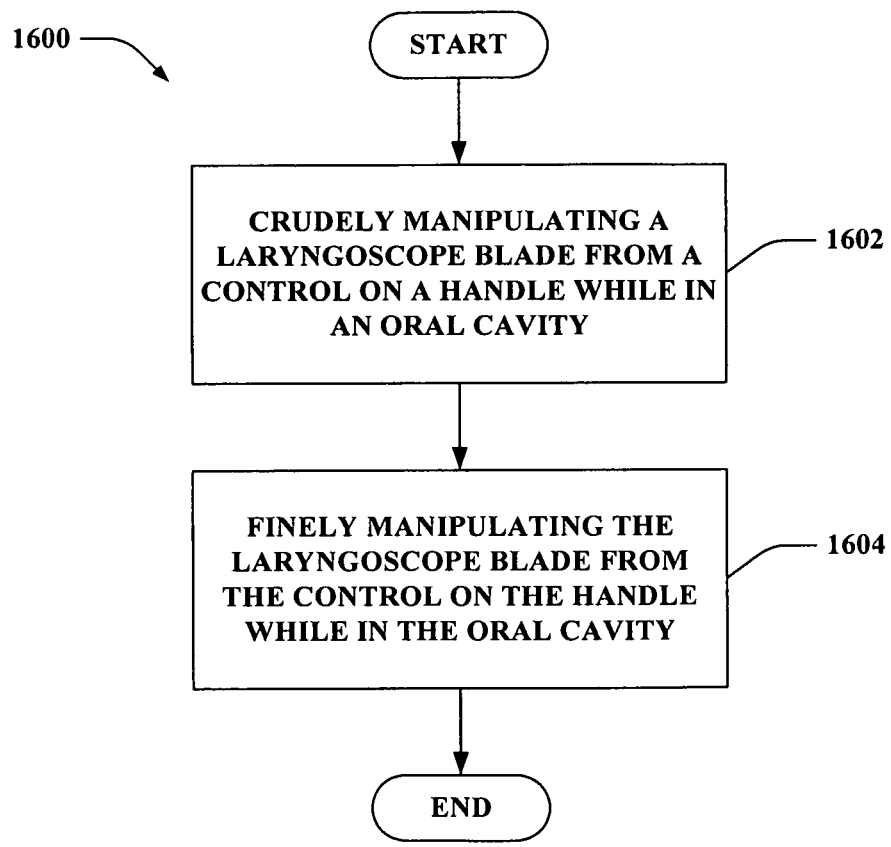
FIG. 16 illustrates an exemplary methodology that enables utilizing a laryngoscope with an articulating blade.
Figure 17:
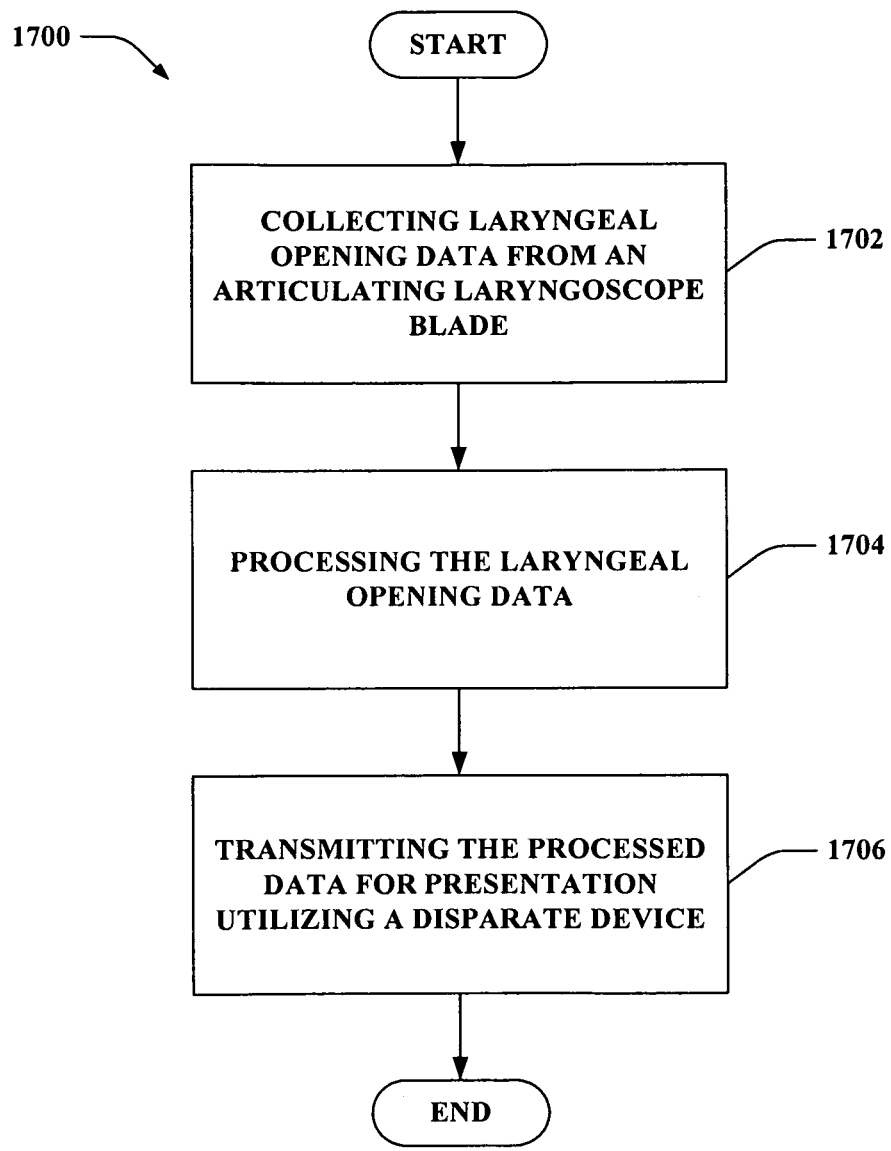
FIG. 17 illustrates an exemplary methodology that facilitates presenting data related to intubation upon an external device in real time.

FIGS. 16-17 illustrate methodologies in accordance with the claimed subject matter. For simplicity of explanation, the methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodologies in accordance with the claimed subject matter. In addition, those skilled in the art will understand and appreciate that the methodologies could alternatively be represented as a series of interrelated states via a state diagram or events.

Referring to FIG. 16, illustrated is a methodology 1600 that enables utilizing a laryngoscope with an articulating blade. At 1602, a laryngoscope blade can be crudely manipulated from a control on a handle while in an oral cavity. The laryngoscope blade can be articulated to position one or more cameras included with the laryngoscope blade (e.g., incorporated into the blade, mounted upon the blade, . . . ) at the base of the tongue looking upwards towards the vocal cords. In contrast to conventional techniques where manipulation of the blade is conducted while outside of the oral cavity, manipulation of the laryngoscope blade can occur within the oral cavity in connection with the claimed subject matter; thus, repeated removal and reinsertion of the blade can be mitigated. At 1604, the laryngoscope blade can be finely manipulated from the control on the handle while in the oral cavity. The fine articulation, for example, can enable moving a tip of the blade to move the epiglottis, thereby yielding a clearer view of the vocal cords. It is contemplated that the crude and fine manipulation of the laryngoscope blade can be effectuated mechanically, via an electric signal, and so forth.

Turning to FIG. 17, illustrated is a methodology 1700 that facilitates presenting data related to intubation upon an external device in real time. At 1702, laryngeal opening data can be collected from an articulating laryngoscope blade. For example, data can be obtained utilizing digital cameras mounted upon and/or incorporated into the articulating laryngoscope blade. Further, the blade can be maneuvered to position the cameras with a clear view to the vocal cords. At 1704, the laryngeal opening data can be processed. For instance, data from a plurality of digital cameras can be combined to yield a stereoscopic view of the vocal cords. At 1706, the processed data can be transmitted for presentation utilizing a disparate device. The data can be transmitted wirelessly, for instance. Moreover, the processed data can be transferred to any type of disparate device that can yield an output. Thus, for example, the processed data can be sent wirelessly to a monitor in an operating room, a cell phone, a PDA, etc. Further, the disparate device can render an output in real time. Accordingly, as the laryngoscope blade is articulated within the oral cavity, a display can be rendered upon the disparate device in real time that shows a view of the vocal cords from the base of the tongue.

Figure 18:
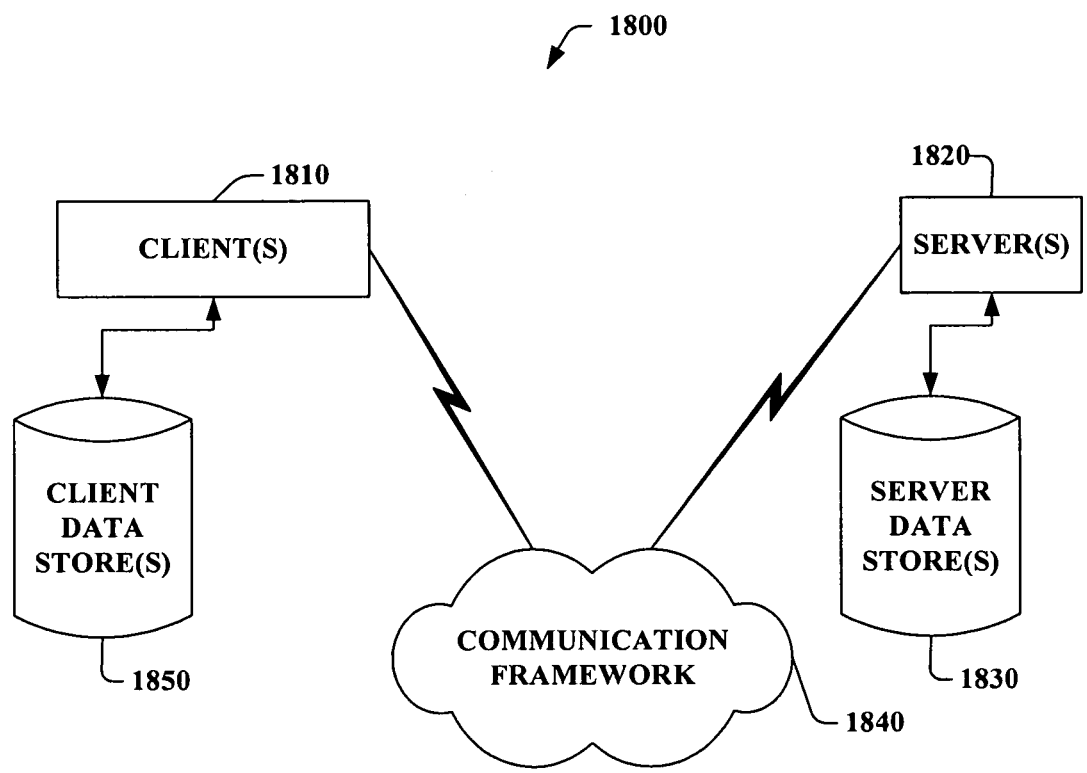
FIG. 18 illustrates an exemplary networking environment, wherein the novel aspects of the claimed subject matter can be employed.
Figure 19:
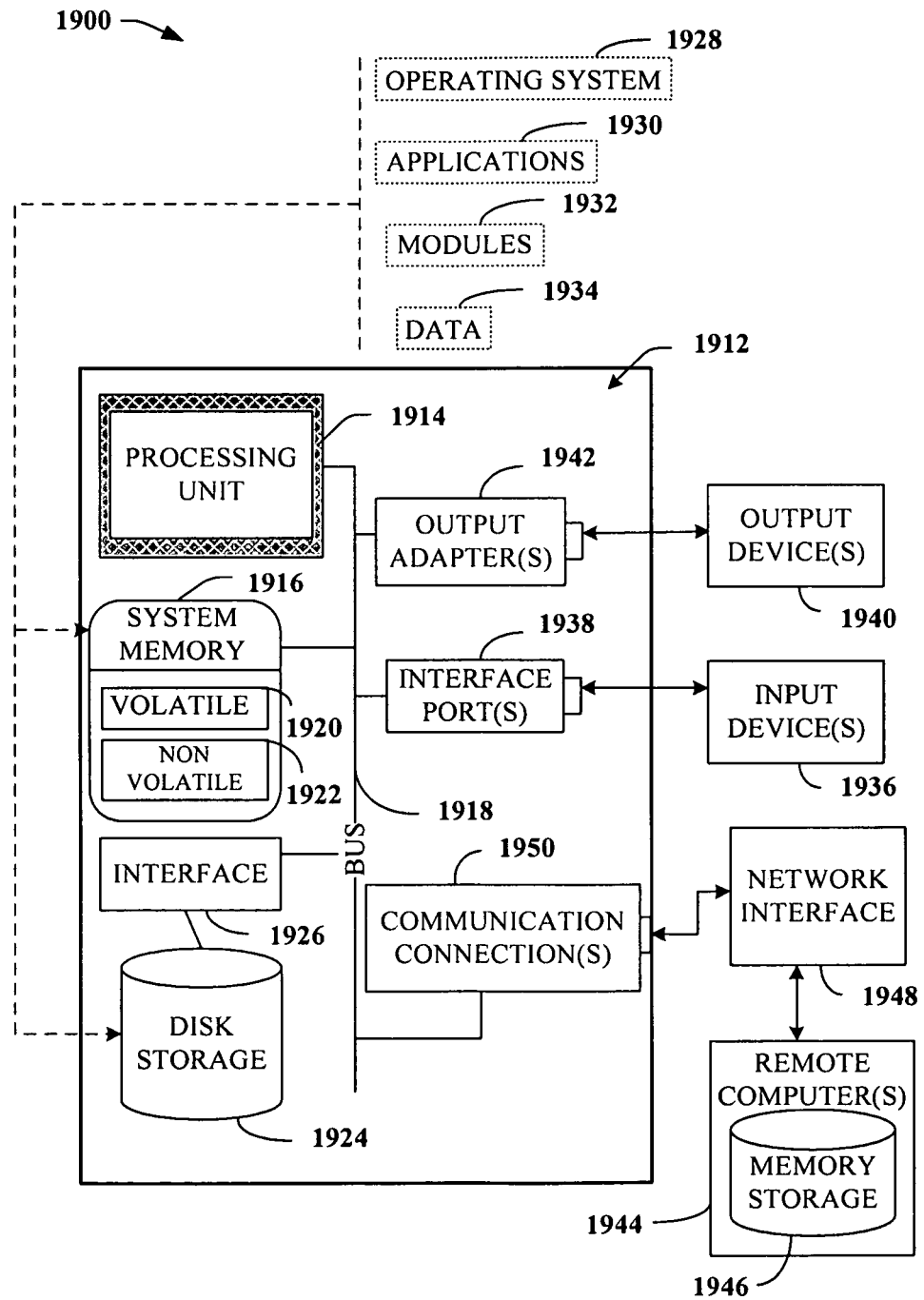
FIG. 19 illustrates an exemplary operating environment that can be employed in accordance with the claimed subject matter.

In order to provide additional context for implementing various aspects of the claimed subject matter, FIGS. 18-19 and the following discussion is intended to provide a brief, general description of a suitable computing environment in which the various aspects of the subject innovation may be implemented. For instance, FIGS. 18-19 set forth a suitable computing environment that can be employed in connection with generating and/or utilizing replicas of states. While the claimed subject matter has been described above in the general context of computer-executable instructions of a computer program that runs on a local computer and/or remote computer, those skilled in the art will recognize that the subject innovation also may be implemented in combination with other program modules. Generally, program modules include routines, programs, components, data structures, etc., that perform particular tasks and/or implement particular abstract data types.

Moreover, those skilled in the art will appreciate that the inventive methods may be practiced with other computer system configurations, including single-processor or multi-processor computer systems, minicomputers, mainframe computers, as well as personal computers, hand-held computing devices, microprocessor-based and/or programmable consumer electronics, and the like, each of which may operatively communicate with one or more associated devices. The illustrated aspects of the claimed subject matter may also be practiced in distributed computing environments where certain tasks are performed by remote processing devices that are linked through a communications network. However, some, if not all, aspects of the subject innovation may be practiced on stand-alone computers. In a distributed computing environment, program modules may be located in local and/or remote memory storage devices.

FIG. 18 is a schematic block diagram of a sample-computing environment 1800 with which the claimed subject matter can interact. The system 1800 includes one or more client(s) 1810. The client(s) 1810 can be hardware and/or software (e.g., threads, processes, computing devices). The system 1800 also includes one or more server(s) 1820. The server(s) 1820 can be hardware and/or software (e.g., threads, processes, computing devices). The servers 1820 can house threads to perform transformations by employing the subject innovation, for example.

One possible communication between a client 1810 and a server 1820 can be in the form of a data packet adapted to be transmitted between two or more computer processes. The system 1800 includes a communication framework 1840 that can be employed to facilitate communications between the client(s) 1810 and the server(s) 1820. The client(s) 1810 are operably connected to one or more client data store(s) 1850 that can be employed to store information local to the client(s) 1810. Similarly, the server(s) 1820 are operably connected to one or more server data store(s) 1830 that can be employed to store information local to the servers 1820.

With reference to FIG. 19, an exemplary environment 1900 for implementing various aspects of the claimed subject matter includes a computer 1912. The computer 1912 includes a processing unit 1914, a system memory 1916, and a system bus 1918. The system bus 1918 couples system components including, but not limited to, the system memory 1916 to the processing unit 1914. The processing unit 1914 can be any of various available processors. Dual microprocessors and other multiprocessor architectures also can be employed as the processing unit 1914.

The system bus 1918 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1916 includes volatile memory 1920 and nonvolatile memory 1922. The basic input/output system (BIOS), containing the basic routines to transfer information between elements within the computer 1912, such as during start-up, is stored in nonvolatile memory 1922. By way of illustration, and not limitation, nonvolatile memory 1922 can include read only memory (ROM), programmable ROM (PROM), electrically programmable ROM (EPROM), electrically erasable programmable ROM (EEPROM), or flash memory. Volatile memory 1920 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM).

Computer 1912 also includes removable/non-removable, volatile/nonvolatile computer storage media. FIG. 19 illustrates, for example a disk storage 1924. Disk storage 1924 includes, but is not limited to, devices like a magnetic disk drive, floppy disk drive, tape drive, Jaz drive, Zip drive, LS-100 drive, flash memory card, or memory stick. In addition, disk storage 1924 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1924 to the system bus 1918, a removable or non-removable interface is typically used such as interface 1926.

It is to be appreciated that FIG. 19 describes software that acts as an intermediary between users and the basic computer resources described in the suitable operating environment 1900. Such software includes an operating system 1928. Operating system 1928, which can be stored on disk storage 1924, acts to control and allocate resources of the computer system 1912. System applications 1930 take advantage of the management of resources by operating system 1928 through program modules 1932 and program data 1934 stored either in system memory 1916 or on disk storage 1924. It is to be appreciated that the claimed subject matter can be implemented with various operating systems or combinations of operating systems.

A user enters commands or information into the computer 1912 through input device(s) 1936. Input devices 1936 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1914 through the system bus 1918 via interface port(s) 1938. Interface port(s) 1938 include, for example, a serial port, a parallel port, a game port, and a universal serial bus (USB). Output device(s) 1940 use some of the same type of ports as input device(s) 1936. Thus, for example, a USB port may be used to provide input to computer 1912, and to output information from computer 1912 to an output device 1940. Output adapter 1942 is provided to illustrate that there are some output devices 1940 like monitors, speakers, and printers, among other output devices 1940, which require special adapters. The output adapters 1942 include, by way of illustration and not limitation, video and sound cards that provide a means of connection between the output device 1940 and the system bus 1918. It should be noted that other devices and/or systems of devices provide both input and output capabilities such as remote computer(s) 1944.

Computer 1912 can operate in a networked environment using logical connections to one or more remote computers, such as remote computer(s) 1944. The remote computer(s) 1944 can be a personal computer, a server, a router, a network PC, a workstation, a microprocessor based appliance, a peer device or other common network node and the like, and typically includes many or all of the elements described relative to computer 1912. For purposes of brevity, only a memory storage device 1946 is illustrated with remote computer(s) 1944. Remote computer(s) 1944 is logically connected to computer 1912 through a network interface 1948 and then physically connected via communication connection 1950. Network interface 1948 encompasses wire and/or wireless communication networks such as local-area networks (LAN) and wide-area networks (WAN). LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1950 refers to the hardware/software employed to connect the network interface 1948 to the bus 1918. While communication connection 1950 is shown for illustrative clarity inside computer 1912, it can also be external to computer 1912. The hardware/software necessary for connection to the network interface 1948 includes, for exemplary purposes only, internal and external technologies such as, modems including regular telephone grade modems, cable modems and DSL modems, ISDN adapters, and Ethernet cards.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable medium having computer-executable instructions for performing the acts and/or events of the various methods of the claimed subject matter.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," and "including" and variants thereof are used in either the detailed description or the claims, these terms are intended to be inclusive in a manner similar to the term "comprising."

What is claimed is:

1. A device, comprising:
    a display;
    a memory that stores computer executable components; and
    a processor that executes at least the following computer executable components stored in the memory:
        a link component configured to connect with a plurality of different medical devices via a wireless or wired connection to facilitate operation of the different medical devices and to transfer data between the device and the different medical devices;
        a proximity recognition component configured to automatically identify a medical device of the different medical devices when the device comes within a wireless transmission range of the medical device;
        a configuration component configured to automatically configure the device to facilitate operation of the medical device in response to identification thereof by the proximity recognition component;
        an interaction component configured to generate a graphical user interface comprising a menu with various modes via which the device can facilitate the operation of the medical device, including a diagnostic mode and a prognostic mode;
        an input component configured to receive user input selecting one of the various modes, wherein in response to selection of the one of the various modes, the device is configured to provide functionality corresponding to the one of the different modes; and
        a control component configured to receive a command based on the one of the various modes and wirelessly provide the command to the medical device when the device is connected to the medical device to control operations of the medical device.

2. The device of claim 1, wherein the proximity recognition component is further configured to decipher operational characteristics of the medical device within the wireless transmission range of the device.

3. The device of claim 1, further comprising:
    a camera configured to capture a picture of a medical condition, and wherein the computer executable components further comprise:
    a data analysis component configured to perform pattern recognition upon the picture, wherein the pattern recognition is a first round of evaluation based on a preliminary scan of the picture.

4. The device of claim 1, wherein the link component is configured to receive data captured by the medical device in response to the command, and wherein the computer executable components further comprise:
    a search component configured to initiate a search for additional information based on the data using one or more external databases.

5. The device of claim 1, wherein the medical device includes a robotic arm, and wherein the control component is configured to apply the command to the robotic arm to effectuate movement of the robotic arm.

6. The device of claim 1, wherein the interaction component is configured to select the various modes via which the device can facilitate the operation of the medical device based on a user profile.

7. The device of claim 1, wherein the device is configured to physically connect to at least one of the different medical devices, the device further comprising:
    a motor configured to drive operation of the at least one of the different medical devices based on instruction provided by the control component.

8. The device of claim 7, wherein the motor is a servomotor.

9. The device of claim 8, wherein the at least one of the different medical devices includes a flexible scope comprising a transducer and wherein the servomotor is configured to control operation of the transducer.

10. The device of claim 7, wherein the at least one of the different medical devices includes a flexible scope configured to insert into a human body, wherein the flexible scope comprises a camera configured to capture image data of the human body when inserted therein and send the image data to the device for processing thereof, wherein the device further comprises:
    an analysis component configured to identify a target based on analysis of the image data, and wherein the control component is configured to automatically control operation of the motor to guide the flexible scope to the target.

11. The device of claim 7, wherein the at least one of the different medical devices includes a laryngoscope with an articulating blade and a camera associated with the articulating blade, wherein the articulating blade and the camera are configured to move independently based on the instruction provided by the control component.

12. A tangible computer-readable storage medium comprising computer-readable instructions that, in response to execution, cause a computing device to perform operations using a processor, the operations comprising:
    communicatively coupling the computing device to a medical device to enable operation of the medical device by the computing device, including transfer of data between the computing device and the medical device, based on a determination that the computing device is capable of enabling operation of the medical device;
    generating a graphical user interface comprising a menu with various modes via which the computing device can facilitate operation of the medical device, including a diagnostic mode and a prognostic mode;
    receiving user input selecting one of the various modes, wherein in response to selection of the one of the various modes, the computing device is configured to provide functionality corresponding to the one of the different modes;
    receiving a command based on the user input associated with the one of the various modes; and
    wirelessly providing the command to the medical device to control operations of the medical device.

13. The tangible computer-readable storage medium of claim 12, wherein the operations further comprise:
    receiving medical data from the medical device in response to the command, wherein the medical data comprises image data of at least a portion of a human body;
    evaluating the image data, including identifying a pattern in the image data and comparing the pattern to patterns corresponding to known medical conditions; and determining a preliminary diagnosis of a medical condition based on the evaluating.

14. The tangible computer-readable storage medium of claim 13, wherein the operations further comprise:
transmitting the medical data and information identifying the preliminary diagnosis through a wireless connection to a medical service provider;
receiving final diagnosis information through the wireless connection from the medical service provider based on the transmitting; and
rending the final diagnosis information via a display of the computing device.

15. The tangible computer-readable storage medium of claim 13, wherein the operations further comprise:
generating a referral for a physician in response to a determination that the preliminary diagnosis of the medical condition warrants the referral.

16. The tangible computer-readable storage medium of claim 15, wherein the generating the referral comprises selecting the physician based on the preliminary diagnosis, medical record data associated with the human body, and an insurance plan associated with the human body.

17. The tangible computer-readable storage medium of claim 12, wherein the medical device comprises a home testing device configured to measure a medical parameter associated with at least a portion of a human body in response to the command, wherein the operations further comprise:
receiving the medical parameter from the medical device in response to the command; and
analyzing the medical parameter to facilitate diagnosing a medical state or condition associated with the medical parameter.

18. The tangible computer-readable storage medium of claim 12, wherein the communicatively coupling the computing device to the medical device is responsive to establishment of a physical or a wired connection between the computing device and the medical device.

19. The tangible computer-readable storage medium of claim 12, wherein the connecting to the medical device further comprises:
detecting the medical device in response to the medical device being within a wireless transmission range of the computing device;
establishing a wireless connection between the computing device and the medical device; and
automatically configuring the computing device to facilitate operation of the medical device in response to the establishing the wireless connection.

* * * * *